(12) United States Patent
Furste et al.

(10) Patent No.: US 6,605,713 B1
(45) Date of Patent: Aug. 12, 2003

(54) MIRROR-SYMMETRICAL SELECTION AND EVOLUTION OF NUCLEIC ACIDS

(76) Inventors: Jens Peter Furste, Witzelbenplatz 5, 14507 Berlin (DE); Rolf Bald, Gustav-Muller-Str. 46, 10829 Berlin (DE); Volker A. Erdmann, Argentinische Allee 2, 14163 Berlin (DE)

(*) Notice: Subject to any disclaimer, the term of this patent is extended or adjusted under 35 U.S.C. 154(b) by 0 days.

(21) Appl. No.: 09/254,126

(22) PCT Filed: Aug. 29, 1997

(86) PCT No.: PCT/EP97/04726
§ 371 (c)(1),
(2), (4) Date: Apr. 29, 1999

(87) PCT Pub. No.: WO98/08856
PCT Pub. Date: Mar. 5, 1998

(30) Foreign Application Priority Data

Aug. 30, 1996 (EP) .............................. 96113953

(51) Int. Cl.[7] .......................... C07H 21/00; C12P 19/34
(52) U.S. Cl. .......................... 536/25.3; 435/6; 435/91.1
(58) Field of Search ................ 435/6, 5, 91.1; 536/25.3, 23.1, 24.5; 514/44

(56) References Cited

U.S. PATENT DOCUMENTS 5,780,221 A * 7/1998 Schumacher et al. .......... 435/5

FOREIGN PATENT DOCUMENTS

| WO | WO 96 34879 A | 11/1996 |
|---|---|---|
| WO | WO 97 43444 A | 11/1997 |

OTHER PUBLICATIONS

Ashley, Gary W. Journal of the American Chemical Society, vol. 114, No. 25, pp. 9731–3736.*
Damha et al. Tetrahedron Letters, vol. 32, No. 23, pp. 2573–2576.*
A. Holy, A synthesis of 2'–Deoxy–L–Uridine. Tetrahedron Letters, vol. (2), pp. 189–192, 1971.*
Crooke, S., Basic Principles of Antisense Therapeutics, Springer–Verlag Berlin Heidelberg New York, Jul. 1998.*
Gura T., Antisense Has Growing Pains, Science, vol. 270, pp. 575–577, Oct. 1995.*
Crooke, S. et al., Antisense '97: A roundtable on the state of the industry, Nature Biotechnology, vol. 15, p. 522, Jun. 1997.*
Branch, A., A good antisense molecule is hard to find, TIBS vol. 23, pp 47–49, Feb. 1998.*
Garbesi, et al. "L–DNAs as Potential Antimessenger Oligonucleotides: a Reassessment", Nucleic Acids Research, 1993, vol. 21, No. 18, 4159–4165.
Anderson, et al. "Preparation and Characterization of Oligonucleotides of D– and L–2' Deoxyuridine" Nucleosides & Nucleotides, 3(5), 499–512 (1984).

Damha, et al., "Oligodeoxynucleotides Containing Unnatural L–2'–Deoxyribose" Tetrahedron Letters, vol. 32, No. 23, pp. 2573–2576, 1991.
Urata, et al., "Mirror–Image DNA", J. Am. Chem. Soc. 1991, 113, 8174–8175.
Morvan, et al., "Sugar Modified Oligonucleotides. III (1). Synthesis, Nuclease Resistance and Base Pairing Properties of alpha– and beta–L–Octathymidylates", Biochemical and Biophysical Research Communications, vol. 172, No. 2, 1990, 537–543.
Bloomers, et al., "Effects of the Introduction of L–Nucleotides into DNA. Solution Structure of the Heterochiral Duplex d (G–C0G–(L)T–G–C–G) d (C–G–C–A–G–C) Studies by NMR Spectroscopy", Biochemistry 1994, 33, 7886–7896.
Asseline, et al., "Synthesis and Physicochemical Properties of Oligonucleotides Built with Either alpha–L or Beta–L Nucleotides Units and Covalently Linked to An Acridine Derivative", Nucleic Acids Research, vol. 19, No. 15, 4067–4074.
Kieninger, et al., "Computer Simulation of Antisense DNA Containing Enantio–deoxynucleotides in the Double Helix", Anti–Cancer Drug Design, 1995, 10, 189–201.
Visser, et al., "Synthesis of the Mirror Image of the RNA Fragment D–CAAGG: A Model Compound to Study Interactions Between Oligonucleotides of Opposite Handedness", Recl. Trav. Chim Pays–Bas 105, 528–537 (1986).
Gary A. Ashley, "Modeling, Synthesis, and Hybridization Properties of (L)–Ribonnucleic Acid", J. Am. Chem. soc., vol. 114, No. 25, 1992.
Schumacher TNM et al, "Identification of D–Peptide Ligands Through Mirror–Image Phage Display", Mar. 29, 1996, *Science* 271:1854–1857.
Urata et al., "Synthesis and Properties of Mirror–Image DNA", 1992, *Nucleic Acid Research* 20(13): 3325–3332.
Bock. Louias C. et al., "Selection of single–stranded DNA molecules that bind and inhibit human thrombin", Feb. 6, 1992 *Nature* 355:564–566.
Ellington, Andrew D. et al., "In vitro selection of RNA molecules that bind specific ligands", Aug. 30, 1990, *Nature* 346:818–822.

(List continued on next page.)

*Primary Examiner*—Sean McGarry
*Assistant Examiner*—Janet L. Epps-Ford
(74) *Attorney, Agent, or Firm*—John R. Wetherell, Jr.; Pillsbury Winthrop LLP

(57) ABSTRACT

A method is disclosed for identifying and producing L-nucleic acids which interact with a target molecule having a natural configuration, as well as the L-nucleic acids produced by this method. Also disclosed is the use of D-nucleic acids which bind to the optical antipode of the target molecule as a matrix for producing L-nucleic acids with an identical sequence, and pharmaceutical compositions and kits which contain the disclosed L-nucleic acids.

40 Claims, 23 Drawing Sheets

OTHER PUBLICATIONS

Figure 6:
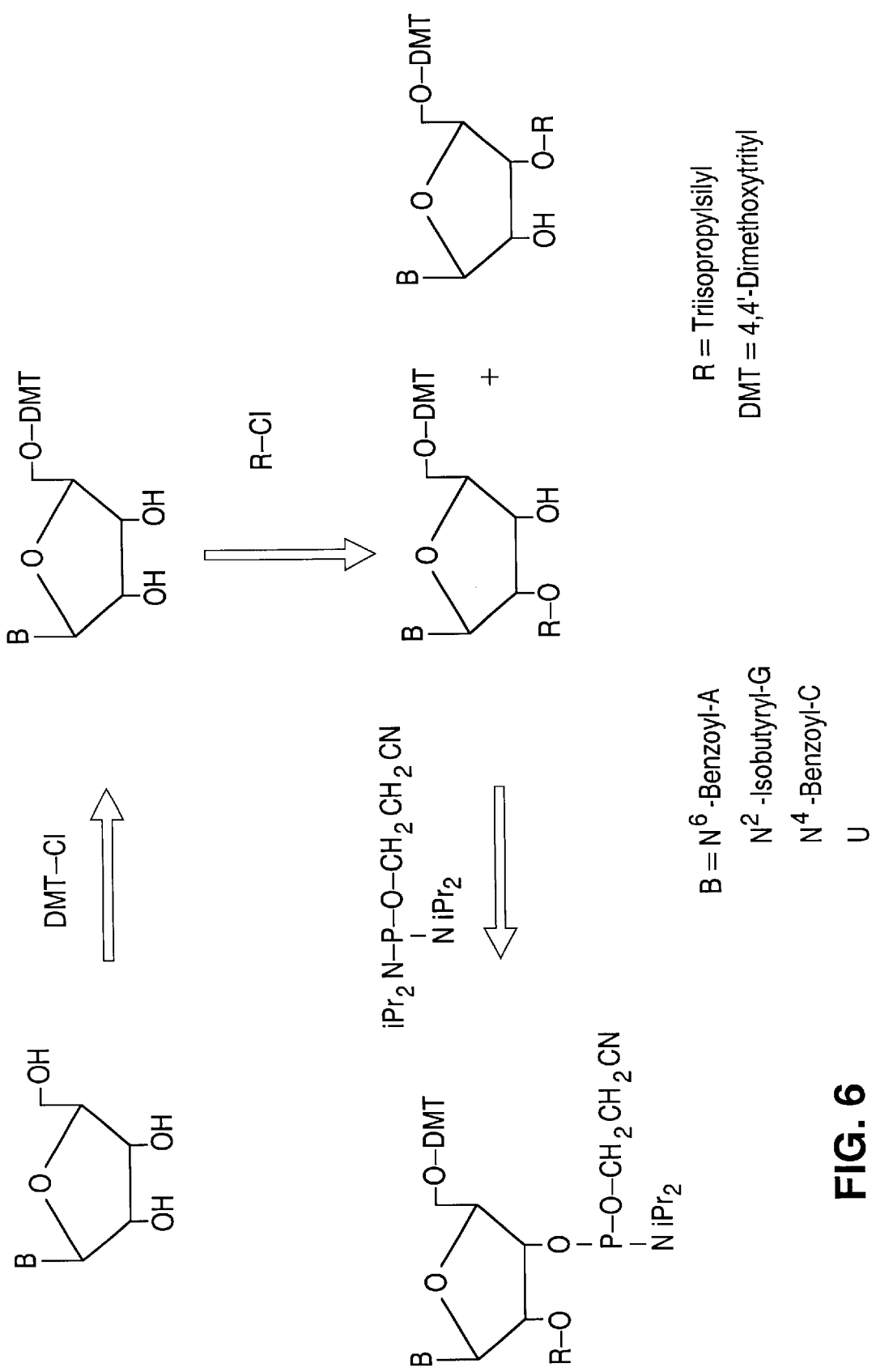

Gold, Larry, "Oligonucleotides as Research, Diagnostic, and Therapeutic Agent", Jun. 9, 1995, *The Jlnl of Biological Chemistry* 270(23):13581–13584.

Klußmann et al., "Mirror–image RNA that binds D–adenosine", 9/96, *Nature Biotechnology* 14:1112–1115.

Lorsch, Jon R. et al., "In vitro evolution of new ribozymes with polynucleotide kinase activity" Sep. 1, 1994, *Nature* 371:31–36.

Milton, R.C. deL, et al. "Total Chemical Synthesis of a D–Enzyme: The Enantiomers of HIV–1 Protease Show Demonstration of Reciprocal Chiral Substrate Specificity", Jun. 5, 1992, *Science* 256:1445–1448.

Nolte et al., "Mirror–design of L–oligonecleotide ligands binding toL–arginine", 9/96, *Nature Biotechnology* 14:1116–1119.

* cited by examiner a) Chemical synthesis of the DNA matrix
b) Amplification by polymerase chain reaction (PCR)
c) In vitro transcription
d) Selection by specific binding
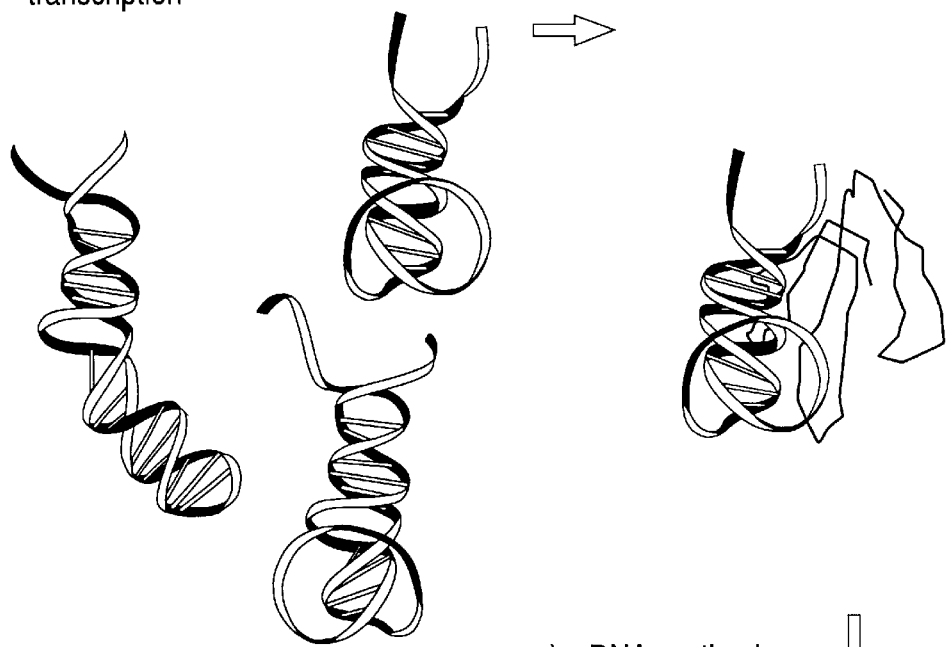
e) cDNA snythesis
f) Complementary strand synthesis
FIG. 1 a) Population of heterogeneous D-RNA (or D-DNA)
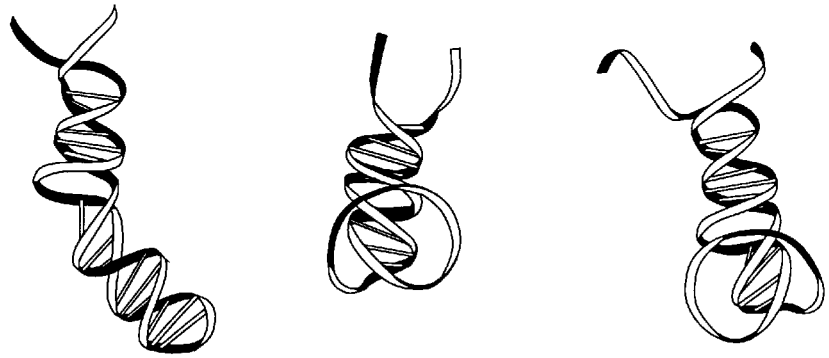
b) Selection by specific binding to the optical antipode of the target molecule
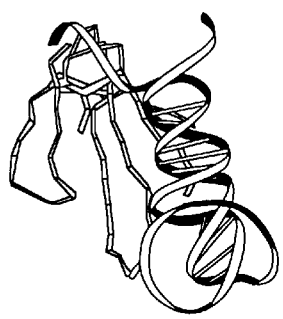
c) Sequencing of the selected variants
d) Chemical synthesis of L-RNA (or L-DNA) by use of sequence information obtained
e) Specific binding of L-RNA (or L-DNA) to the target molecule
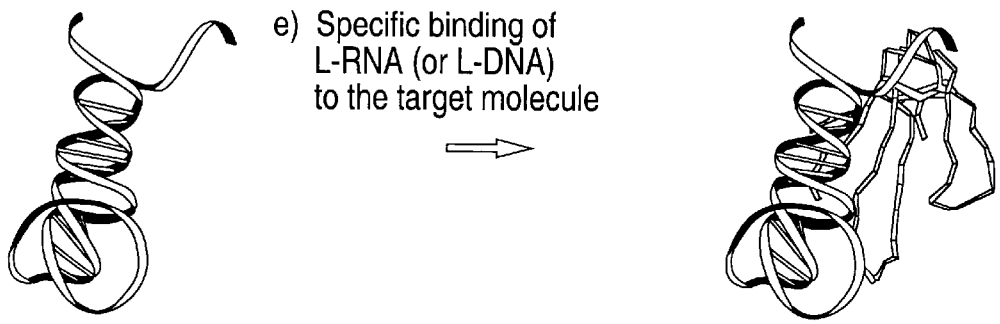
FIG. 2 a) Population of heterogeneous D-RNA (or D-DNA)
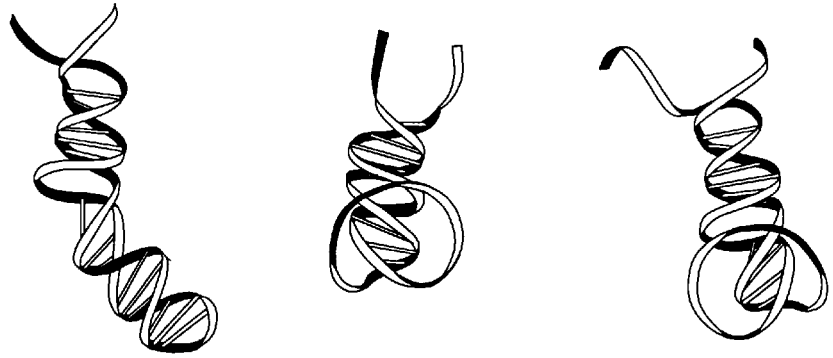
b) Selection by specific binding to the optical antipode of the target molecule
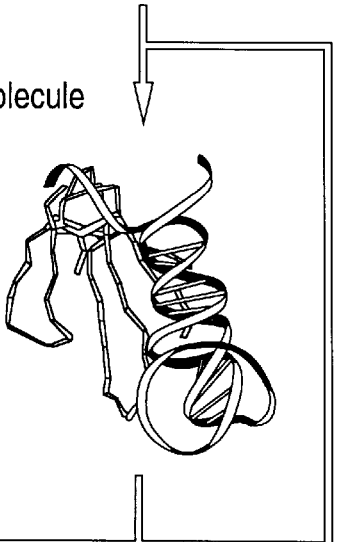
c) Amplification (variation)
d) Sequencing of the selected variants
e) Chemical synthesis of L-RNA (or L-DNA) by use of sequence information obtained
f) Specific binding of L-RNA (or L-DNA) to the target molecule
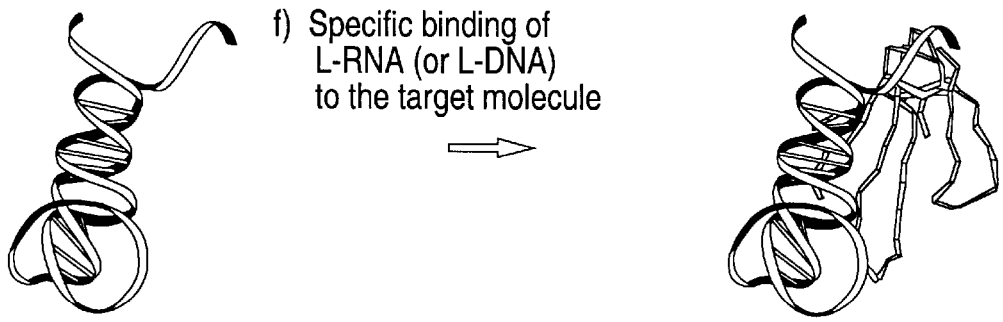
FIG. 3 a) Population of heterogeneous L-RNA (or L-DNA)
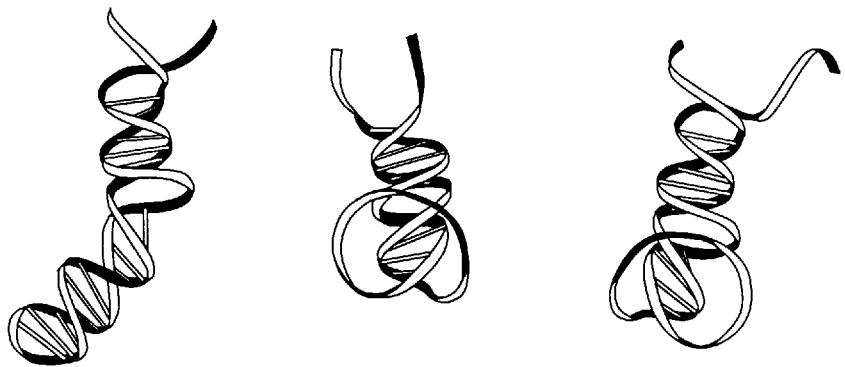
b) Selection by specific binding to the target molecule
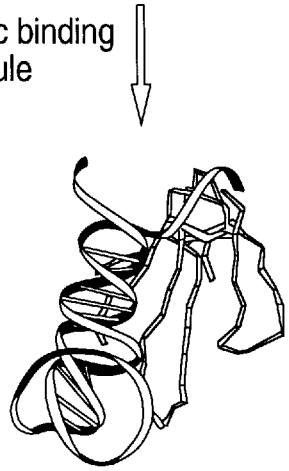
c) Sequencing of the selected variants
d) Chemical or enzymatical synthesis of L-RNA (or L-DNA)
e) Specific binding of L-RNA (or L-DNA) to the target molecule
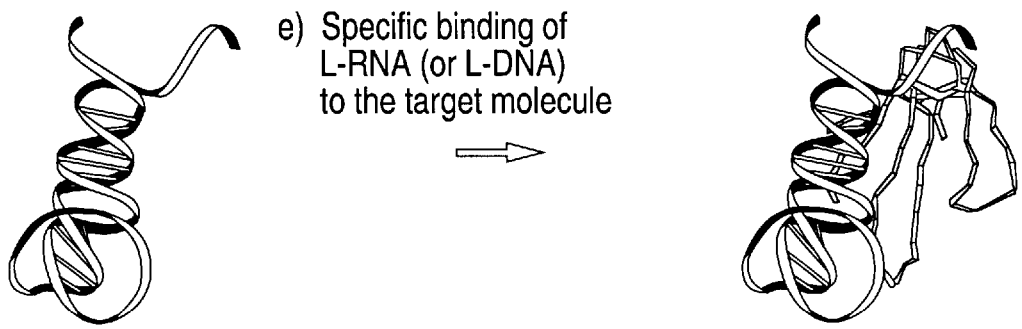
FIG. 4 a) Population of heterogeneous L-RNA (or L-DNA)
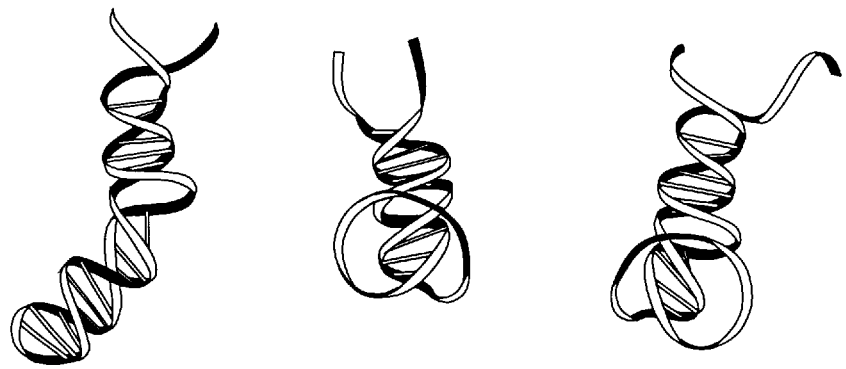
b) Selection by specific binding to the target molecule
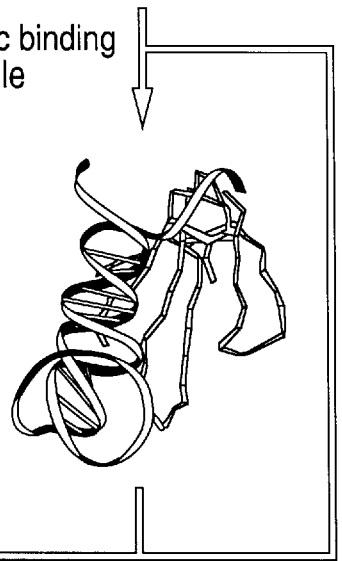
c) Amplification (variation)
d) Sequencing of the selected variants
e) Chemical or enzymatical synthesis of L-RNA (or L-DNA)
f) Specific binding of L-RNA (or L-DNA) to the target molecule
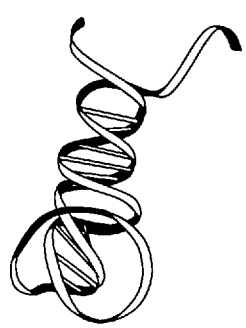
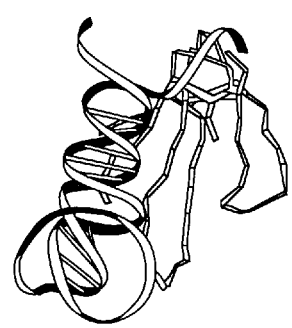
FIG. 5

FIG. 12

|  | Box I | | Box II | | Box III | |
|---|---|---|---|---|---|---|
| D-A10 5'-$N_{18}$ | ccGCAAAA | cTTATTAG---·········· | AA | CCTGAATAGATATTCAGG---·········· | CGAATG | TACTGAGCCGTTGTCTctgcaggc-$N_{12}$-3' |
| D-A24 5'-$N_{18}$ | ccGCAAAA | ACACCTAGTGT---·········· | AA | CCCTCCATAGCGTGGG---·········· | CGAATG | TAAAGAGCTCACCCCATGCctgca-$N_{16}$-3' |
| D-A42 5'-$N_{18}$ | ccGCAAAA | GCGTTTTTCGC---·········· | AT | ACCGTATTCGTTATAGGGT---·········· | CGATTG | TAACGAGCTCTGCTCCctgcaggc-$N_{12}$-3' |
| D-A45 5'-$N_{18}$ | ccGCAAAA | GTCTTTATGAC---·········· | AA | TCCTGGTAGGA---·········· | CGATTG | TACCGAAGCTCAATCACGGATCTC-$N_{20}$-3' |
| D-A91 5'-$N_{18}$ | ccGCAAAA | CGGAGCATTGTGATCCG---·········· | AA | GTCGCTAATCGAGTGAC---·········· | CGACTG | TACTGAGCATCCCctgcaggcatgc-$N_{9}$-3' |
| D-A12 | CCGCAAAA | GGCTTTATGTC---·········· | AT | CTG-$N_{20}$-3' 5'-$N_{20}$-CTAGCAAGCCTAAGCAGCAG | CGAATG | GAACAGTTTC-- |
| D-A83 | CCGCAAAA | GCATAGTTCTGCGCctgcaggc | gca-$N_7$-3' 5'-$N_{18}$-gctcggtaccTATCCCTCGC | CGAATG | TCTTTGCCATTGCAATAGA-- |
| consensus | CCGCAAAA | | AW | | CGAHTG | |

| Competitor | $K_d c$ ($\mu M$) | $K_d c / K_d D\text{-}A$ |
| --- | --- | --- |
| D-adenosine | 2.2 ± 0.1 | 1 |
| 3'-O-methyl-D-adenosine | 1.4 ± 0.2 | 0.6 |
| D-guanosine | 4.8 ± 0.5 | 2.2 |
| 3'-deoxy-D-adenosine | 8.0 ± 0.4 | 3.6 |
| 2'-deoxy-D-adenosine | 1400 ± 100 | 640 |
| D-uridine | 2300 ± 100 | 1050 |
| D-adenosine triphosphate | 2900 ± 1500 | 1320 |
| D-cytidine | 6200 ± 200 | 2800 |
| 2'-O-methyl-D-adenosine | 12900 ± 1300 | 5900 |
| Adenine | 16300 ± 1100 | 7400 |
| L-adenosine | 20100 ± 1700 | 9100 |

FIG. 18

FIG. 20

```
AB91 5'-N20-GGCTCATTGCCTGTTGCCTGGCAAAATGATATTAATCA--------------------------AAACCGAGTTCTTCGGT----------------------CGAATGctgcaggcatgcagcttgg------NO-3'
AB92 5'-N13-cgg tacc GCCGGAGTACCGGAAAACGGGAAACCG----------------------AACTAGTAGATAGCGTATACTAG--------------CGATTGTAGTctgcaggcatgcaagcttgg-NO-3'
AB93 -----------CAGGCCGCAAAAAGAC tgcagg-N19-3' 5'-N20-TGCCGTCTAAGTGATCCAGGTGATGAC---------------CGAATGCCTGAGCATTAT-------
CONSENSUS             CGGCAAAA                                        AW                                      CGAHTG
```

FIG. 29

MIRROR-SYMMETRICAL SELECTION AND EVOLUTION OF NUCLEIC ACIDS

The present invention relates to methods for identifying and producing L-nucleic acids that interact with a target molecule having a natural configuration, as well as to the L-nucleic acids produced by means of this method. Furthermore, the invention relates to the use of the D-nucleic acids binding to the optical antipode of the target molecule as a matrix for producing L-nucleic acids with an identical sequence, as well as to pharmaceutical compositions, kits, diagnostic agents and sensor systems containing the L-nucleic acids of the invention.

In the past few years, new technologies have been established in order to use nucleic acids in a manner previously unanticipated. Among these are, e.g., the use of such molecules as catalysts, inhibitors or stimulators of biochemical reactions that take place within or outside of the cell. There is hardly any doubt that these technologies will in the future play a dominant role in the fields of medicine, pharmaceutical diagnostics, biotechnology and agriculture.

An essential part of some of the new DNA and RNA techniques is in vitro selection or evolution (cf. for example the review article of J. W. Szostak, TIBS 17 (1992), 89 to 93, Famulok and Szostak, Angew. Chemie 104 (1992), 1001–1011 and Gold et al., Annu. Rev. Biochem. (1995)). These techniques are based on the working methods of biological systems. Thereby, novel DNA and RNA molecules with desired properties may be obtained from a combinatorial library of heterogeneous nucleic molecules by means of variation, selection and replication. Thus, such an in vitro system contains all factors present in biological evolution. It may rightfully be referred to as an in vitro evolution which many times accelerates the speed of natural methods. As long as no additional variation steps occur in this system, it is no in vitro evolution, but merely an in vitro selection method.

From a group of up to $10^{18}$ different RNA species, the RNA molecules with highly affine binding properties or catalytic properties may be isolated by means of a cyclic process of the polymerase chain reaction (PCR), transcription, selective binding and reverse transcription; cf. Gold et al., loc. cit. One of the essential advantages of this method is the fact that it is not necessary to know the structure of the molecule to be selected; molecules with the "correct" structure are filtered out from the starting population by means of a selection step and, if desired, they may subsequently be sequenced. The principle of this selection or evolution process is schematically depicted in FIG. 1.

Examples for such in vitro selection or evolution methods have been provided by Tuerk and Gold, Science 249 (1990), 505–510, Berzal-Herranz et al., Genes & Development 6 (1992), 129–134 and by Robertson and Joyce, Nature 344 (1990), 467–468. These work groups successfully selected functional ribonucleic acids cleaving or binding a predetermined nucleic acid differing from the substrate by means of slightly varying experimental approaches. In a more recent study, Lehmann and Joyce have shown that a ribozyme's metal ion specificity may be changed from Mg2+ to Ca2+ by such an in vitro evolution process (Nature 361 (1993), 182–185).

Highly affine RNA, but also DNA, molecules may not only be constructed for the purpose of interaction with other nucleic acids, but primarily for their interacting with proteins, with other, smaller molecules of the cell or with synthetic compounds. Attempts may also be made for interactions with the cellular receptors or with viral particles. Usually, such interactions of highly affine nucleic acids have the purpose of inhibiting or stimulating a biological function or of prompting a signal in sensor systems.

The advantage of nucleic acid libraries when compared to combinatorial libraries of other oligomers or polymers may be found in the dual nature of nucleic acids. The molecules possess a genotype (a sequence capable of propagation) and a phenotype (a functional structure). This enables the amplification of functional molecules from very large combinatorial libraries and their identification by means of sequencing. The additional labeling of the molecule library in order to identify functional variants e.g. by "tagging" (Janda, Proc. Natl. Acad. Sci. USA 91 (1994), 10779–10785) and the technical problems associated therewith (Gold et al., loc. cit.; Gold, J. Biol. Chem. 270 (1995), 13581–13584) may be avoided. By using combinatorial phage libraries in order to identify peptide motifs (Scott and Smith, Science 249 (1990), 386–390, Devlin et al., Proc. Natl. Acad. Sci. USA (1990), 6378–6382), which also involves the combination of genotype and phenotype, other disadvantages occur. Whereas oligonucleotides with only 25 nucleotides may already form very stable structures, comparable oligopeptides possess large conformational liberties (Gold et al., loc. cit.). The structural liberty of peptides and the entropic disadvantages in the interaction with target structures resulting therefrom limit the possibilities of using peptides, as long as high affinities and specificities are necessary for the application of the molecules. This limitations also occur in the selection of biologically stable D-peptides by means of phage libraries (Schumacher et al., Science 271 (1996); 1854–1857). The use of cyclic peptides may not offset these basic disadvantages (Gold et al., loc. cit.).

The particular disadvantage in using combinatorial nucleic acid libraries instead of other oligomers or polymers is the low stability of nucleic acids in biological liquids.

However, all selection and evolution processes known so far are only capable of producing highly affine or catalytic RNAs or DNAs in natural form, i.e. with D-ribose or D-deoxyribose as a basic component. During use in a biological environment these molecules are degraded by enzymes. The degradation leads to a short term of effect of these highly affine or catalytic nucleic acids.

Although it is possible after the selection of unmodified nucleic acids to introduce a targeted modification in order to slow down the enzymatic degradation, the influence of this modification on the structure and thereby on the functionality of the nucleic acids may, however, not be predicted. Furthermore, altered, undesired properties cannot be anticipated. In addition, the degradation of chemically modified DNAs or RNAs leads to products that may influence the cell metabolism in a serious and disadvantageous manner in the form of analogues of nucleosides, nucleotides or oligonucleotides.

It is furthermore possible to integrate into the process modified nucleoside triphosphates which increase the stability of the nucleic acids. Examples for this procedure have been described by Jellinek et al., Biochemistry 34 (1995), 11363–11372. and Eaton and Pieken, Annu. Rev. Biochem. 64 (1995), 837–863. As the nucleoside triphosphates must be compatible to the polymerases used, the range of possible modifications is very limited. Furthermore, it has to be expected that the degradation of these modified nucleic acids leads to particularly toxic effects.

Thus, the technical problem underlying the present invention was to provide processes, by means of which highly affine nucleic acid molecules can be produced via in vitro selection or evolution, which do not exhibit the above-described disadvantages mentioned in the prior art. This technical problem is solved by the embodiments characterized in the claims. Thus, the present invention relates to a process for producing L-nucleic acids interacting with a target molecule having natural configuration, said process comprising the following steps:

(a) producing a heterogeneous population of D-nucleic acids;

(b) bringing the population mentioned in step (a) into contact with the optical antipode of the target molecule;

(c) separating the D-nucleic acids interacting with the optical antipode of the target molecule;

(d) sequencing the D-nucleic acids interacting with the optical antipode of the target molecule;

(e) synthesizing L-nucleic acids, the sequences of which are identical with the sequences of the D-nucleic acids determined in step (d).

In this context, an "L-nucleic acid" may be any nucleic acid occurring in the naturally not occurring L-configuration. This means that instead of an D-ribose or D-deoxyribose, which naturally form the backbone of a nucleic acid, L-ribose or L-deoxyribose are used as the basic component of the L-nucleic acids. The term "a target molecule having natural configuration" may comprise any molecule capable of binding a nucleic acid, as long as it occurs in its natural structure. Examples for such molecules are proteins composed of L-amino acids, L-amino acids, nucleic acids consisting of D-nucleotides, as well as D-sugars and more complex sugar molecules consisting thereof.

The production of a heterogeneous D-nucleic acid population may be carried out by any means of processes known in the prior art. Examples for such processes are the amplification of genomic fragments (Kinzler and Vogelstein., Nucl. Acids Res. 17 (1989), 3645–3635) or the chemical solid phase synthesis of DNA molecules by means of synthesizers (Thiesen and Bach, Nucl. Acids Res. 18 (1990), 3203–3209 and Pollock and Treisman, Nucleic Acids Res. 18 (1990), 6197–6204). Moreover, the skilled person is capable of varying these processes, depending on the experimental arrangement, which also lead to the desired results. The nucleic acids may consist of a desired number of D-nucleotides. The D-nucleotides preferably exhibit arbitrary (not previously determined) nucleotides in at least 15 positions.

The heterogeneous D-nucleic acid population exhibits any desired number of members, preferably of at least $10^9$ members.

In step (b), the D-nucleic acids are brought into contact with the optical antipode of the target molecule, allowing for the interaction of the (highly) affine nucleic acid with the optical antipode of the target molecule.

In this context, the term "optical antipode of the target molecule" means the enantiomeric form of a (macro) molecule occurring in natural configuration. The optical antipode of the target molecule can be produced according to methods described in the prior art. Thus, for example Orata et al. (Nucl. Acids Res. 20 (1992), 3325 to 3332) have described the synthesis of a hexadeoxyribonucleotide consisting of L-deoxyriboses. Furthermore, the L-nucleic acids may be produced as described in Example 1. The optical antipode of a L-(poly)peptide may for example be produced according to the processes described by Milton et al. (Science 258 (1992), 1445–1448) or Muir (Structure 3 (1995), 649–652).

The separation of D-nucleic acids not interacting with the target molecule takes place according to processes known from the prior art. The separation may be carried out, for example, by means of a column-chromatographic process, whereby the optical antipode of the target molecule is bound to the column material and affine or, as the case may be, highly affine D-nucleic acids are held back under suitable conditions. The nucleic acids bound in such a way can be eluted from the column material after the washing of the unbound nucleic acids. However, the separation may also be carried out by means of separating techniques such as filtering methods or magnetic particles. Moreover, the skilled person is capable of modifying the processes described in the prior art for its own special needs.

After separating the non-interacting nucleic acids from the interacting nucleic acids, the interacting nucleic acids are separated from the optical antipode of the target molecule. Provided that a limited heterogeneity of the population of step (a) had existed and that it may be assumed that a sufficient number of identical or similar molecules occurs, the D-nucleic acids previously interacting with the optical antipode of the target molecule can be directly sequenced. Suitable sequencing techniques are known from the prior art; cf. Sambrook et al., Molecular Cloning, A Laboratory Manual $2^{nd}$ edition, 1989, Cold Spring Harbor Laboratory, Cold Spring Harbor. Provided that in this selection technique nucleic acids with different sequences bind to the optical antipode of the target molecule and are subsequently sequenced, a sequence information may be obtained which is ambiguous at various positions. However, it may be taken into consideration that a number of nucleic acids are conserved at certain positions. This shows their role in the binding of the optical antipode of the target molecule, as was shown by Blackwell et al. (Blackwell and Weintraub, Science 250 (1990), 1104 to 1110, Blackwell et al., Science 250 (1990), 1149 to 1151). This limited information already enables the skilled person to synthesize an L-nucleic acid capable of binding to the desired target molecule.

For many applications, the process of identifying mirror-symmetrical nucleic acids is rather expansive since at first the antipode of the target structure has to be prepared in enantiomerically pure form. The racemat cleaving may be circumvented if the enantiomerically pure target structure is at disposal. In another preferred embodiment the invention therefore relates to a process that causes the interaction of the D-nucleic acids with the racemic mixture of a target molecule. The separation of the D-nucleic acid not interacting with the racemic mixture of the target molecule is carried out according to methods known in the art. The separation may for example take place by means of a column-chromatographic method, whereby the racemic mixture of the target molecule is bound to the column material, and affine or, as the case may be, highly affine D-nucleic acids are held back under suitable conditions.

Hereby, nucleic acids, which may interact (a) with the target structure, (b) the mirror-symmetrical target structure or (c) with both isomers due to the low chiral discrimination, bind at first. The share of highly affine D-nucleic acids bound to the naturally occurring enantiomer and possessing a low chiral specificity may be washed with the natural target molecule by means of elution. The remaining D-nucleic acids bound to the optical antipode may subsequently be specifically eluted with the racemic mixture. Thereby, it is possible to carry out the process of mirror-symmetrical selection or evolution even without isolating the optical antipode of the target molecule.

The synthesis of the L-nucleic acids is carried out according to processes known from the prior art (Urata et al., loc. cit.) or according to the method described in Example 1.

Considering L. Pasteur's studies (e.g. in Soc. Chim. Paris 1860, 1, (1860)) with regard to enantiomers, it may be postulated that the naturally occurring nucleic acids possess optical antipodes the basic component of which is L-ribose or L-deoxyribose. In accordance with the present invention's object, the chemical solid phase synthesis of L-RNA and L-DNA have now successfully been established in any desired sequence (cf. Example 1).

On examining a nucleic acid selected according to the method of the invention, it may be postulated that a corresponding L-polymer of identical sequence interacts with the optical antipode of the target molecule in the same manner. If the enantiomer of the target molecules is utilized in the evolution or selection process, sequence information may be obtained allowing for the production of highly affine or catalytic L-RNAs or L-DNAs. The principle of this method is depicted in FIG. 2. The advantage of this method referred to as mirror-symmetrical selection or evolution is the high stability of the products in biological environment. By means of this method, an L-oligoribonucleotide was for the first time identified, which binds to the naturally occurring D-adenosine with high affinity (cf. Example 2). After incubating the L-oligoribonucleotide in human serum, no degradation could be stated. In subsequent investigations it could be proved that L-oligoribonucleotide only binds D-adenosine and that D-oligoribonucleotide only binds L-adenosine. This shows that D- and L-oligonucleotides with identical, covalently linked nucleotide bonds fold up in the same manner in order to acquire three-dimensional structure, and that the nucleotide sequence only determines the tertiary structure of a nucleic acid. The affinity of L-RNA to D-adenosine described in Example 2 (dissociation factor 1.8 $\mu$M) lies within the range of the affinities of D-RNA to nucleosides achieved so far by means of in vitro evolution (cf. Connell and Yarus, Science 264 (1994), 1137–1141 and Huizenga and Szostak, Biochemistry 34 (1995), 656–665). Thus, it has been shown for the first time that L-nucleic acids are capable of developing equally high affinities to naturally occurring chiral target substances as D-nucleic acids. The principle of the process could be confirmed by the identification of arginine-specific ligands (cf. Example 3).

The mirror-symmetrical evolution or selection exhibits the particular feature that selection takes place with regard to the optical antipode of the target molecule. This particularity has two essential advantages: on the one hand, the optical antipode of the target molecule is not so easily degraded during the process of the invention, as is the case with naturally occurring enantiomers. This feature plays an important role in the case of the target molecule being an RNA. On the other hand, the herein-described method in particular offers an advantage unknown in the prior art, namely, that after the finished selection or evolution procedure the enantiomer of the selected (highly) affine D-nucleic acid is produced.

This L-nucleic acid not only exhibits the above-described high stability in a biological environment which grants its long-termed effect in biological systems. As a consequence of this stability, which is due to the lack of suitable degrading enzymes in biological systems, metabolites of these nucleic acids which might represent a sanitary hazard are no longer formed. Moreover, it is likely that these L-nucleic acids are not or only to small extent dealt with by the immune system and therefore only prompt a slight immune reaction, if any. The products of the process of the invention may therefore be used as pharmaceutical compositions without further hesitation.

Thus, the process of the invention provides products, which are mirror-symmetrical reflections of naturally occurring nucleic acids. These products have a defined sequence and possess a high binding affinity against a given ligand or catalyze a desired reaction at a desired target molecule. Thereby, chemically synthesized polymers are provided which exhibit a high biological stability and may be used analogously to monoclonal antibodies. The versatile hydrolytic properties, but possibly also synthetic properties, render the molecules of the invention interesting for chemical or pharmaceutical uses.

In a further preferred embodiment the invention relates to a process, wherein the following step is additionally added subsequently to step (c):

(ca) amplifying the D-nucleic acids interacting with the optical antipode of the target molecule.

By means of this embodiment of the invention, in particular D-nucleic acids may be selected which are present in the heterogeneous starting population in low numbers. The principle of this preferred embodiment is depicted in FIG. 3. The additional amplification step increases the (highly) affine D-nucleic acids obtained by binding to the optical antipode of the target molecule. Said D-nucleic acids may be further enriched in a repeated selection step or they may be directly sequenced after amplification. Amplifications may, however, also be carried out in isothermal systems. Such systems have e.g. been described by Guatelli et al. (Proc. Natl. Acad. Sci. USA 87 (1990), 1874–1878), and Walker et al. (Nucl. Acids Res. 20 (1992), 1691–1696).

In another preferred embodiment of the process of the invention the D-nucleic acids of the step (a) population exhibit primer binding sites or, as the case may be, complementary sequences to primer binding sites at their 5' and 3' ends, which allow for an amplification by PCR of the D-nucleic acids obtained in step (ca).

This embodiment of the process of the invention is particularly suitable if the D-nucleic acid is selected on an RNA level. Moreover, use can be made of transcription by means of a DNA-dependent RNA polymerase as an additional amplification step apart from PCR. A combination of both these amplification steps thus enables a particularly high yield of D-nucleic acid material interacting with the optical antipode of the target molecule.

In a further preferred embodiment of the process of the invention the following step is added subsequently to step (ca):

(cb) bringing the amplified D-nucleic acids into contact with the optical antipode of the target molecule.

This step is followed by step (b) and possibly (ca) before carrying out step (d), whereby the steps (cb), (b) and possibly (ca) may be repeated in this order once or several times.

The amplification of the D-nucleic acids isolated in the selection steps via PCR leads to the enrichment of the desired D-nucleic acids in a comfortable manner. In a preferred embodiment of the process of the invention, in which several cycles of bringing the amplified D-nucleic acids into contact with the optical antipode of the target molecule, subsequent separating of the unbound molecule (selection) and amplification take place, finally the nucleic acids with the highest binding affinities are selected. By varying the molar ratio of the optical antipode of the target molecule and D-nucleic acids, selection may take place with respect to a majority of (highly) affine D-nucleic acids (ratio >1) or to one or only a few nucleic acids (ratio $\leqq$1). Correspondingly, step (e) results in one or a few highly affine L-nucleic acids or in a majority of (highly) affine L-nucleic acids. The respective results may be achieved by varying the number of selection steps, whereby a high number of selection steps will finally result in one or in a few D-nucleic acids with high binding affinities.

The amplification step of the process of the invention may comfortably be carried out by means of PCR. PCR is a well-established method in the prior art, the principles of which have been described in Sambrook, loc. cit. RNA as well as DNA may be amplified via PCR, whereby a process step resulting in the translation of RNA into a corresponding cDNA by means of reverse transcriptase may be integrated into the amplification of RNA.

However, the amplification may also be achieved by means of other techniques known from the prior art.

In another preferred embodiment of the process of the invention nucleotides are integrated during amplification into the nucleotide strands to be synthesized anew.

These nucleotides do not occur at the nucleotide position of the D-nucleic acids interacting with the target molecule and mentioned in step (a).

By this preferred embodiment selection may take place with regard to novel D-nucleic acid species not occurring in the starting population in a similar manner as in the biological in vivo evolution. Thus, this is a case of in vitro evolution. Several variants of this process are conceivable, all falling under the scope of protection of the present invention.

On the one hand, amplification as such may be carried out via a process exhibiting a certain rate of error during the integration of the nucleotides in the strand to be synthesized anew. PCR is a known process of that kind.

Provided that the binding site necessary for optimal binding exhibits more than about 25 nucleotides, there is a certain probability that the corresponding sequence is not contained in the original population of step (a). This is due to the fact that, starting from a certain length of the nucleotide sequence (laying within the range of 25 nucleotides) not any possible sequence may be contained in this population for reasons of practicability.

In case that the optimal sequence for binding to the antipode of the target molecule is indeed not present within the population of step (a), it may, however, be selected with the process of the invention. This is carried out by first isolating a D-nucleic acid with suboptimal binding affinity from the population (within the population, however, this sequence is the molecule with optimal binding affinity). Subsequently, this sequence is mutagenized during amplification. Such mutagenesis techniques are known from the prior art (cf. for example Light and Lerner, Bioorg. Med. Chem. 3 (1995), 995–967 and Pannekoek et al., Gene 128 (1993), 135–140). Thereby, the complete sequence may be mutagenized. The mutagenized sequence is subjected to further selection steps whereby several amplification, mutagenesis and subsequently selection cycles follow each other until a D-nucleic acid with optimal binding properties has been obtained.

Furthermore, for practical reasons, a short D-nucleic acid exhibiting the optimal binding properties of its population may at first be incorporated. The positions essential for binding are determined by means of methods known from the prior art, and the other nucleotide areas are substituted by longer sections. This procedure is again followed by one or more amplification and selection cycles. The parts of the sequence of the thus-determined molecule with optimal binding properties which are unessential for binding are again substituted by a randomized sequence. This process step has for example been described in W 91/19813 in another context and was there designated as "walking".

In a further embodiment of the present invention L-nucleic acids are made to interact directly with a target molecule having natural configuration. Thus, the invention relates to a method for producing L-nucleic acids comprising the following steps:

(a) producing a heterogeneous population of L-nucleic acids;

(b) bringing the population of step (a) into contact with the target molecule;

(c) separating the L-nucleic acids not interacting with the target molecule;

(d) sequencing the L-nucleic acids interacting with the target molecule;

(e) synthesizing L-nucleic acids the sequence of which is identical to the sequences determined in step (d).

The production of a heterogeneous population of L-nucleic acids takes place according to methods known from the prior art (Urata et al., loc. cit.) or according to the method described in Example 1. After separating the non-interacting L-nucleic acids from the interacting L-nucleic acids, the interacting nucleic acids are separated from the target molecule. The L-nucleic acids are then iteratively singled out according to the method set forth in Example 4. Instead of the L-proteins used in Example 4, D-proteins are used in this process. The optical antipodes of the enzymes may be produced according to methods described by Milton et al. (loc. cit.) or by Muir (loc. cit.). The strands may be separated by means of the method described in Example 4 or by means of any method described in the prior art. Examples for such methods are strand separation gels (Maxam and Gilbert, Proc. Natl. Acad. Sci. 78 (1977), 560–564; Maniatis, loc. cit.) or solid phase sequencing (Hultman et al., Nucl. Acids Res. 17 (1989), 4937–4946, Hultman et al., BioTechniques 10 (1991), 84–93). A further possibility of obtaining a single-stranded DNA after PCR is to utilize a primer with an internal spacer (e.g. polyethylene glycol) (Williams and Bartel, Nucl. Acids Res. 23, (1995), 4220–4221). The L-deoxynucleoside triphosphates and L-dideoxynucleoside triphosphate necessary for sequencing are obtained by chemically synthesizing the L-nucleosides described in Example 1 according to methods described in the prior art for D-nucleosides. In the synthesis of triphosphate, the four L-deoxynucleosides are first phosphorylized at the 5'-position (Yoshikawa et al., Tetrahedron Lett. (50), 1967, 5065–5068). The 5'-monophosphates are then transformed into their 5'-triphosphates (Hoard and Ott, J. Am. Chem. Soc. 87 (1965), 1785–1788). In order to synthesize the L-dideoxynucleotide triphosphates, the L-deoxynucleosides are at first transformed into L-dideoxynucleosides. The synthesis of the pyrimidine-L-dideoxynucleosides may be carried out in a multi-step process according to Horwitz et al. (J. Org. Chem. 32 (1967), 817–818) and Joshi et al. (J. Chem. Soc. (1992), 2537–2544). The guanosine-L-dideoxynucleoside may be synthesized according to Herdewijn et al. (J. Med. Chem. 31 (1988), 2040–2048), and the adenosine-L-dideoxynucleoside may be synthesized according to Chu et al. (J. Org. Chem. 54 (1989), 2217–2225). The four L-dideoxynucleosides obtained thereby are then converted into their respective 5'-triphosphates via the intermediate step of 5'-monophosphates by means of the above-mentioned methods of Yoshikawa et al. (Tetrahedron Lett. 50 (1967), 5065–5068) and Hoard and Ott (Hoard and Ott, J. Am. Chem. Soc. 87 (1965), 1785–1788). In a further preferred embodiment the invention relates to a process whereby the following step is additionally introduced after step (c):

(ca) amplifying the L-nucleic acids interacting with the target molecule.

The propagation of the L-nucleic acids is achieved by means of D-polymerases produced according to the methods described by Milton et al. (loc. cit.) or Muir (loc. cit.).

Particularly such L-nucleic acids which are present in low amounts in the heterologous starting population may be selected by this embodiment of the method of the invention. The principle of this preferred embodiment is depicted in FIG. 5. The additional amplification step increases the number of (highly) affine L-nucleic acids obtained by binding to the target molecule. These may be enriched by a repeated selection step or sequenced after amplification.

The amplifications, however, may also be carried out in isothermal systems with the help of corresponding D-polymerases. Such systems have been described for L-polymerases for example by Guatelli et al. (loc. cit.) and Walker et al. (loc. cit.).

In another preferred embodiment of the process of the invention the L-nucleic acids of the step (a) population exhibit primer binding sites or, as the case may be, complementary sequences to primer binding sites at their 5' and 3' ends, which allow for an amplification of the L-nucleic acids obtained in step (ca) obtained by mirror-symmetrical PCR.

This embodiment of the process of the invention is particularly suitable if the L-nucleic acid is selected on an RNA level. Moreover, use can be made of mirror-symmetrical transcription by means of a DNA-dependent D-RNA polymerase as an additional amplification step apart from mirror-symmetrical PCR. A combination of both these amplification steps thus enables a particularly high yield of L-nucleic acid material interacting with the optical antipode of the target molecule.

In a further preferred embodiment of the process of the invention the following step is added subsequently to step (ca):

(cb) bringing the amplified L-nucleic acids into contact with the target molecule.

This step is followed by step (b) and possibly (ca) before carrying out step (d), whereby the steps (cb), (b) and possibly (ca) may be repeated in this order once or several times.

The amplification of the L-nucleic acids isolated in the selection steps via mirror-symmetrical PCR leads to the enrichment of the desired L-nucleic acids in a comfortable manner. In a preferred embodiment of the process of the invention, in which several cycles of bringing the amplified L-nucleic acids into contact with the target molecule, subsequent separating of the unbound molecule (selection) and amplification take place, finally the nucleic acids with the highest binding affinities are selected. By varying the molar ratio of the target molecule and L-nucleic acids, selection may take place with respect to a majority of (highly) affine L-nucleic acids (ratio >1) or to one or only a few nucleic acids (ratio $\leq 1$). Correspondingly, step (e) results in one or a few highly affine L-nucleic acids or in a majority of (highly) affine L-nucleic acids. The respective results may be achieved by varying the number of selection steps, whereby a high number of selection steps will finally result in one or in a few L-nucleic acids with high binding affinities.

In another preferred embodiment of the process of the invention nucleotides are integrated during amplification into the nucleotide strands to be synthesized anew. These nucleotides do not occur at the nucleotide position of the L-nucleic acids interacting with the target molecule and mentioned in step (a). By this preferred embodiment selection may take place with regard to novel L-nucleic acid species not occurring in the starting population in a similar manner as in the biological in vivo evolution. Thus, this is a case of mirror-symmetrical in vitro evolution. Several variants of this process are conceivable, all falling under the scope of protection of the present invention.

In a preferred embodiment the invention relates to a process, whereby the interaction consists in a bond.

In a further preferred embodiment of the process of the invention the interaction consists in a catalytic reaction.

Since the molecules involved in the interaction have to interact with each other before the end of the catalytic reaction, this embodiment also implies an interaction e.g. of the (highly) affine D-nucleic acid with the optical antipode of the target molecule.

Such catalytic reactions have for example been described for ribozymes (cf. e.g. Robertson and Joyce, loc. cit.). Examples for novel catalysts have furthermore been described by Pan and Uhlenbeck (Biochemistry 33 (1994), 9561–9565), as well as by Bartel and Szostak (Science 261 (1993), 1411–1418). Lorsch and Szostak (Nature 371 (1994), 31–36) succeeded in identifying a ribozyme with kinase-activity by means of in vitro selection. Breaker and Joyce (Chem. Biol. 1 (1994), 223–229) have described a novel deoxyribozyme catalyzing the cleavage of a phosphodiester bond, while Cuenoud and Szostak (Nature 375 (1995), 611–614) were able to identify a DNA metaloenzyme with DNA ligase activity.

In another preferred embodiment of the process of the invention the nucleic acids of step (a) are deoxyribonucleic acids.

In a particularly preferred embodiment of the process of the invention the ribonucleic acids are deoxyribozymes.

In a further preferred embodiment of the process of the invention the nucleic acids are ribonucleic acids.

In a particularly preferred embodiment of the process of the invention the ribonucleic acids are ribozymes.

This preferred embodiment of the process of the invention allows for selection of the desired molecules not by binding them to the optical antipode of the target molecule, but also by their catalytic activity. Thus, step (b) of the process of the invention possibly also comprises a cleavage of a substrate which is usually the target molecule or a part thereof, directly in connection with binding to the optical antipode of said target molecule. The cleavage of the substrate may thereby be the starting point for the further amplification and selection of suitable ribozymes. Corresponding systems have been described among others by Robertson and Joyce (loc. cit.).

In a further embodiment of the process of the invention the target molecule is an amino acid, a peptide, a polypeptide or a protein consisting of several polypeptides. The polypeptides or proteins may be glycosylated or unglycosylated.

In accordance with the invention, an amino acid, peptide, polypeptide and protein might be anyone of these (macro) molecules with which the D-nucleic acids or L-nucleic acids (?) are able to interact. Examples for such (macro)molecules are enzymes, structural proteins and hormones. Accordingly, the (macro)molecules may be components of a larger structure or be present in biological systems in diluted form.

In another preferred embodiment of the process of the invention the target molecule is a single-stranded RNA, a double-stranded RNA, a single-stranded DNA or a double-stranded DNA, as well as combinations therefrom.

It is a matter of course for the person skilled in the art that these nucleic acids may assume various conformations under various conditions. The process of the invention comprises any conformation that these (macro)molecules or their combinations might assume. The process of the invention further comprises combinations of these macromolecules. Such combinations may for example consist of single- and double-stranded RNA or DNA or of triple helices.

An antibiotic or a pharmaceutically effective substrate or its pre-stage is the target molecule of a further preferred embodiment of the process of the invention.

Preferred pharmaceutically effective substrates are e.g. steroids, ACE inhibitors, β-blockers and diuretics. Thus, a therapy may effectively be interfered with by means of the L-nucleic acid of the invention and the half-life of an antibiotic or a pharmaceutically effective substrate may successfully be reduced.

In a further preferred embodiment of the process of the invention the target molecule is a sugar molecule, for example a branched or an unbranched polymeric sugar.

The term "sugar molecule" as used herein relates to monomeric as well as to combined complex sugar structures.

In another embodiment of the process of the invention the synthesis of the L-nucleic acid of step (e) takes place in a chemical or enzymatic procedure.

In a particularly preferred embodiment of the process of the invention the chemical synthesis of the L-nucleic acid of step (e) comprises the following steps:
(ea) synthesizing L-nucleosides;
(eb) synthesizing protected L-nucleoside phosphoramidites; and
(ec) solid phase synthesis of L-nucleic acids in a synthesizer.

The invention further relates to L-nucleic acids specifically binding to a target molecule as described above.

The L-nucleic acids of the invention are preferably produced by the process of the invention. Moreover, the L-nucleic acids of the invention may be produced by any variation of the process of the invention, provided that only the selection step utilizing the optical antipode of the target molecule and the synthesizing step utilizing a D-nucleic acid as a matrix are used.

The L-nucleic acids of the invention may be used in various different ways. Due to the high affinity for the target molecule they may be used in a similar manner as monoclonal antibodies. For example, they may be provided with a marker or with a cytotoxic group. The L-nucleic acids of the invention may be used in order to stimulate or inhibit the biological function of a target molecule. Furthermore, the L-nucleic acids may be coupled to a carrier and be used as affinity material for the purifying or separating the target molecules. Immobilized L-nucleic acids may e.g. be used in order to separate enantiomers or enantiomeric impurities. Furthermore, they may be used for the purification and/or separation of cellular factors or cells. According to what is known about DNA sequences it is, e.g., possible to employ corresponding optical antipodes (D-proteins or D-peptides) derived from the protein sequences in the process of the invention and thereby specifically produce affinity materials. Immobilized L-nucleic acids may furthermore be used as affinity material in order to separate cellular factors or cells such as in the separation of toxic components by means of dialysis.

In a particularly preferred embodiment the L-nucleic acid of the invention is L-ribonucleic acid. This L-ribonucleic acid may be present in single- or double-stranded form.

In another particularly preferred embodiment the L-nucleic acid of the invention is a ribozyme.

The present invention for the first time describes a highly affine L-oligoribonucleotide or L-oligodeoxyribonucleotide (cf. Example 1). The L-RNA identified by the process binds specifically to the D-adenosine (cf. Example 2) or L-arginine (cf. Example 3). Comparative experiments have shown that the D-form of these highly affine L-oligoribonucleotides binds the corresponding enantiomeric form of adenosine (cf. Example 2) or arginine (cf. Example 3). Thus, it could be proven that both enantiomeric forms of the highly affine oligoribonucleotide may fold up to acquire a three-dimensional structure in exactly the same manner. Thus, Pasteur's predictions (loc. cit.) concerning the biological activity of optical enantiomers could be confirmed.

In a further particularly preferred embodiment the L-nucleic acid of the invention is an L-deoxyribonucleic acid.

As already mentioned in connection with the L-ribonucleic acids of the invention, the L-deoxyribonucleic acid may be present in single or double stranded form.

In a further particularly preferred embodiment the L-nucleic acid of the invention is a deoxyribozyme.

The invention further comprises the use of the D-nucleic acids obtained in step (c) and/or step (ca) as a matrix for the production of an L-nucleic acid with an identical nucleic acid sequence.

The invention further comprises pharmaceutical compositions containing an L-nucleic acid obtained by the above-described methods or one of the above-described L-nucleic acids, possibly in combination with a covalent modification and/or a pharmaceutically acceptable carrier.

The pharmaceutical compositions of the invention may be used in many different ways. As a matter of course, however, the effective range of the pharmaceutical composition depends on the specificity of the L-nucleic acid. The pharmaceutical compositions of the invention may for example be used in the treatment of cancer, viral and bacterial infections and high blood pressure. In every case, the physician in charge decides about the respective manner of application, dose and duration of treatment, whereby the seriousness of the disease as well as the patient's age and general condition are some of the parameters to be considered by the physician in charge. If deemed necessary, the L-nucleic acid of the invention is dispensed in combination with a pharmaceutically acceptable carrier. The choice of additives depends, among other things, on the form of application. The person skilled in the art, however, knows from the prior art which carrier is to be added to the respective pharmaceutical composition.

Finally, the invention relates to a kit and to a diagnostic agent containing a L-nucleic acid obtained by the above-described methods or an above-described L-nucleic acid. The kit of the invention may be used for diagnostic and analytic purposes. Since, as described above, the L-nucleic acids of the invention may be used in a similar manner as antibodies, the person skilled in the art has the complete range of diagnostic possibilities of polyclonal or monoclonal antibodies at his disposal in order to use them as a field of application of the kit of the invention. The L-nucleic acid of the kit of the invention may for example be provided with a marker and for the in vitro proof of the target molecule.

L-nucleic acids may also be used as biosensors in connection with, e.g. surface-plasma-resonance-sensors, evanescent field sensors or grit coupling agents. Thus, the use of the L-nucleic acids obtained by the process of the invention or of the L-nucleic acids of the invention as biosensors are a further subject matter of the invention: it is also conceivable that the L-nucleic acids may be used as herbicides, additives in foodstuffs, for analytic methods such as determining odorous and/or taste substances or for cosmetic uses such as in anti-aging creams or sun lotions.

This and other embodiments have been disclosed to the person skilled in the art. They are obvious to her/him and comprised by the description and the examples of the present invention. For example, further literature concerning one of the above-mentioned methods, means and uses which may be applied in the sense of the present invention can be seen from the prior art, such as public libraries by using e.g. electronic auxiliary means. For this purpose, other public databases such as "Medline", to be accessed via Internet, may be consulted. Other databases and addresses are known to the person skilled in the art and may be taken from the Internet. A summary of sources and informations concerning biotechnological patents or patent applications is given in Berks, TIBTECH 12 (1994), 352–364.

The Figures show:

FIG. 1: Design of highly affine RNAs. In step (a) at first a heterogeneous DNA matrix is produced. The synthesis of this matrix may be carried out by means of chemical methods. The matrix, however, may for example also consist of a cleavage product of naturally produced DNA and primers for PCR linked thereto via a ligating reaction. In subsequent step (b) the matrix is amplified by PCR. The DNAs obtained in such a way are transcribed in step (c) and subsequently brought into contact with the target molecule. (Highly) affine RNAs bind to the target molecule. After separating the unbound molecules the (highly) affine RNAs are in vitro transcribed into cDNA by means of reverse transcriptase. In step (f), the complementary cDNA strand is finally synthesized, whereby again a double stranded cDNA molecule is obtained. This molecule can then again be amplified and selected with respect to specific binding.

FIG. 2: Mirror-symmetrical selection: in step (a) a population of heterogeneous D-DNAs or D-RNAs is provided. In step (b), these are brought into contact with the optical antipode of the target molecule. D-nucleic acids interacting with the optical antipode of the target molecule are separated from the other D-nucleic acids (selection). Provided that a sufficiently high amount with a relatively homogeneous composition interacts with the optical antipode of the target molecule, these may be sequenced according to the strategy described by Blackwell et al. (loc. cit.). Micro-sequencing methods are described for example by Davis et al. (Genet. Anal. Tech. Appl. 8 (1991), 1–7) and Harding and Keller (Trends Biotechnol. 10 (1992), 55–57). The corresponding L-DNA or L-RNA can be synthesized with the help of the obtained sequence information (step d). This L-DNA or L-RNA will then specifically interact with the target molecule (step e).

FIG. 3: Mirror-symmetrical selection or evolution: These process steps correspond to those depicted in FIG. 2, with the exception that the selected material is amplified after the selection step (b). If errors occur in the amplified material during the de novo cDNA or RNA synthesis, i.e. the amplified material is more heterogeneous than the starting population with respect to the sequence information, the amplification step also contains a variation step. Thus, all forces propelling biological evolution are united in vitro in the system.

FIG. 4: Mirror-symmetrical selection with L-nucleic acids. Mirror-symmetrical selection with L-nucleic acids: In step (a) a population of heterogeneous L-DNAs or L-RNAs are provided. In step (b), these are brought into contact with the target molecule. L-nucleic acids interacting with the target molecule are separated from the other L-nucleic acids (selection). Provided that a sufficiently high amount of L-nucleic acids with a relatively homogeneous composition interacts with the optical antipode of the target molecule, these may be sequenced according to the strategy described by Blackwell et al. (loc. cit.), whereby corresponding L-proteins are substituted by D-proteins. Microsequencing methods have been described for example by Davis et al. (loc. cit.), as well as Harding and Keller (loc. cit.). The corresponding L-DNA or L-RNA may be synthesized with the help of the obtained sequence information (step d). This L-DNA or L-RNA will then specifically interact with the target molecule (step e).

FIG. 5: Mirror-symmetrical selection or evolution. The process steps correspond to those depicted in FIG. 3, except for the modification that a population of heterogeneous L-nucleic acids is provided and the L-proteins used are substituted by D-proteins. The sequence informations can be determined after iterative in vitro isolation (see Example 4).

FIG. 6: L-ribophosphoramidite synthones.

Figure 7:
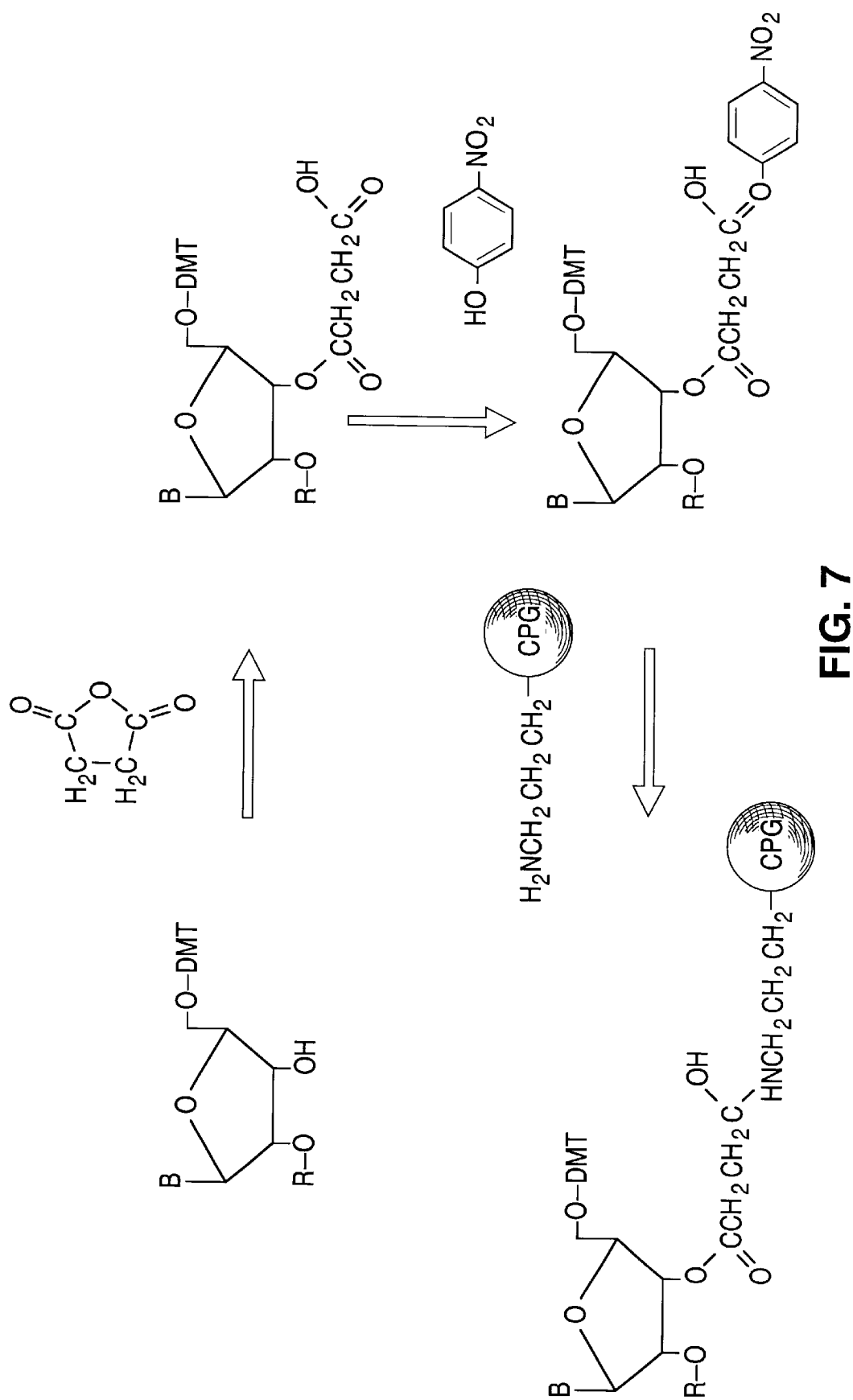

FIG. 7: Synthesis of carrier-bound L-ribonucleosides (protected).

Figure 8:
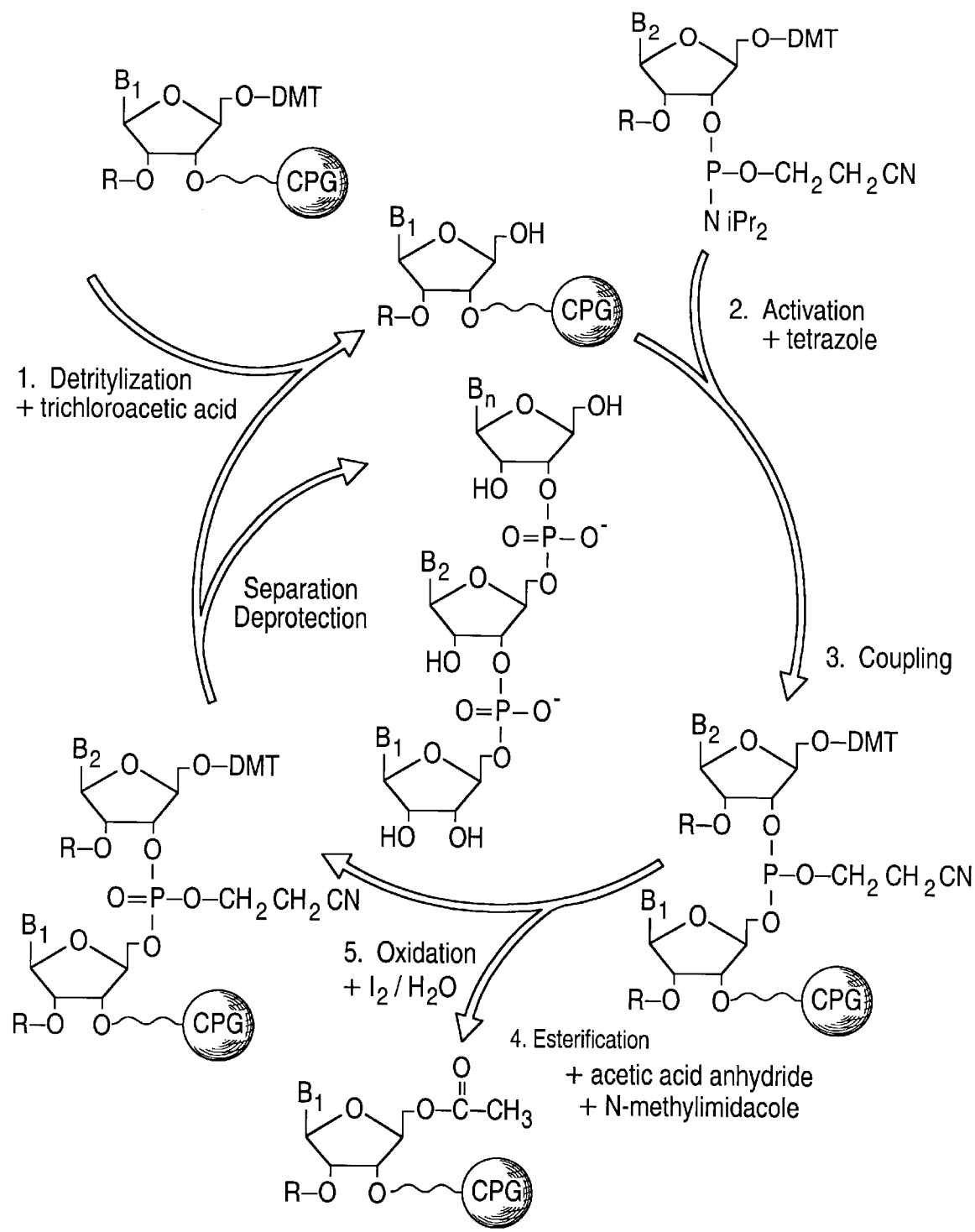

FIG. 8: Solid phase synthesis of L-RNA.

Figure 9:
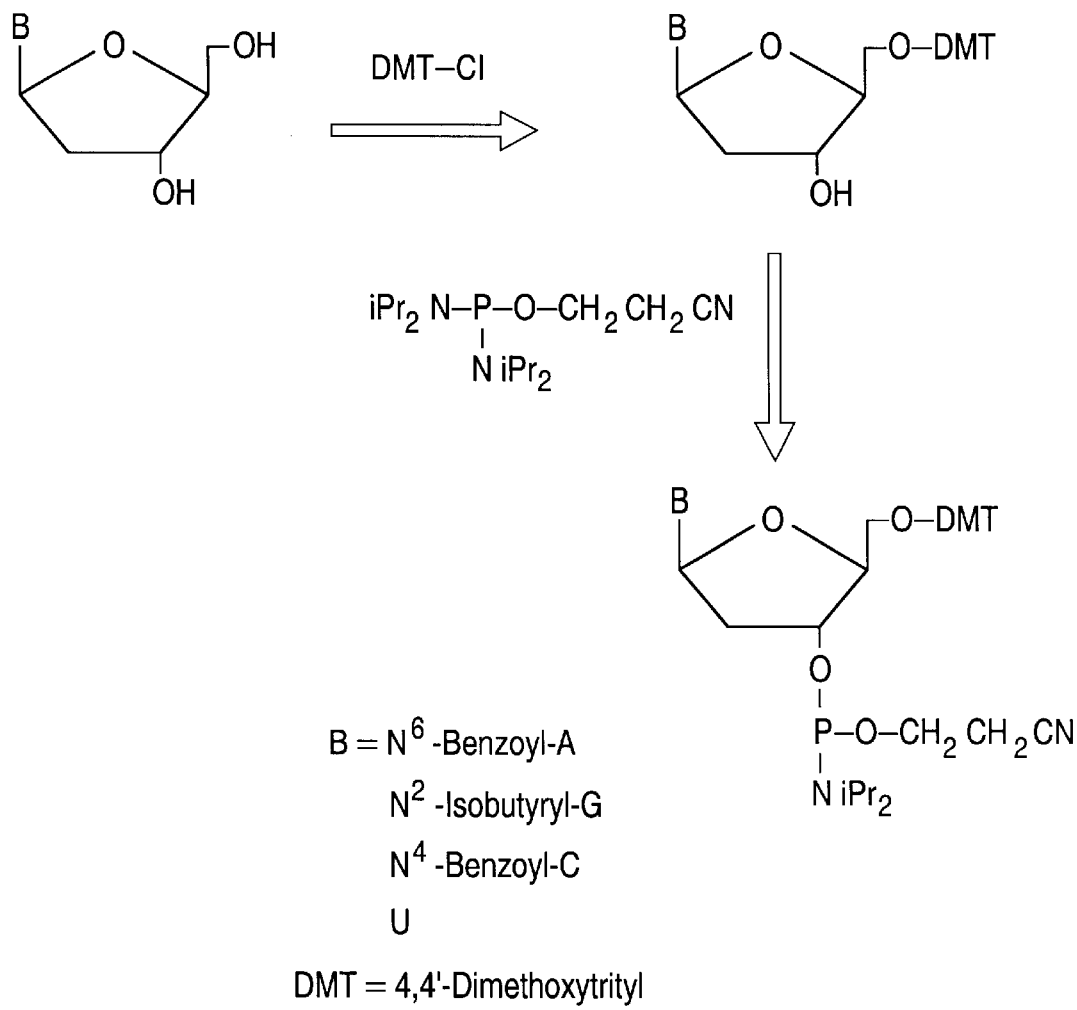

FIG. 9: L-deoxyribophosphoramidite synthones.

Figure 10:
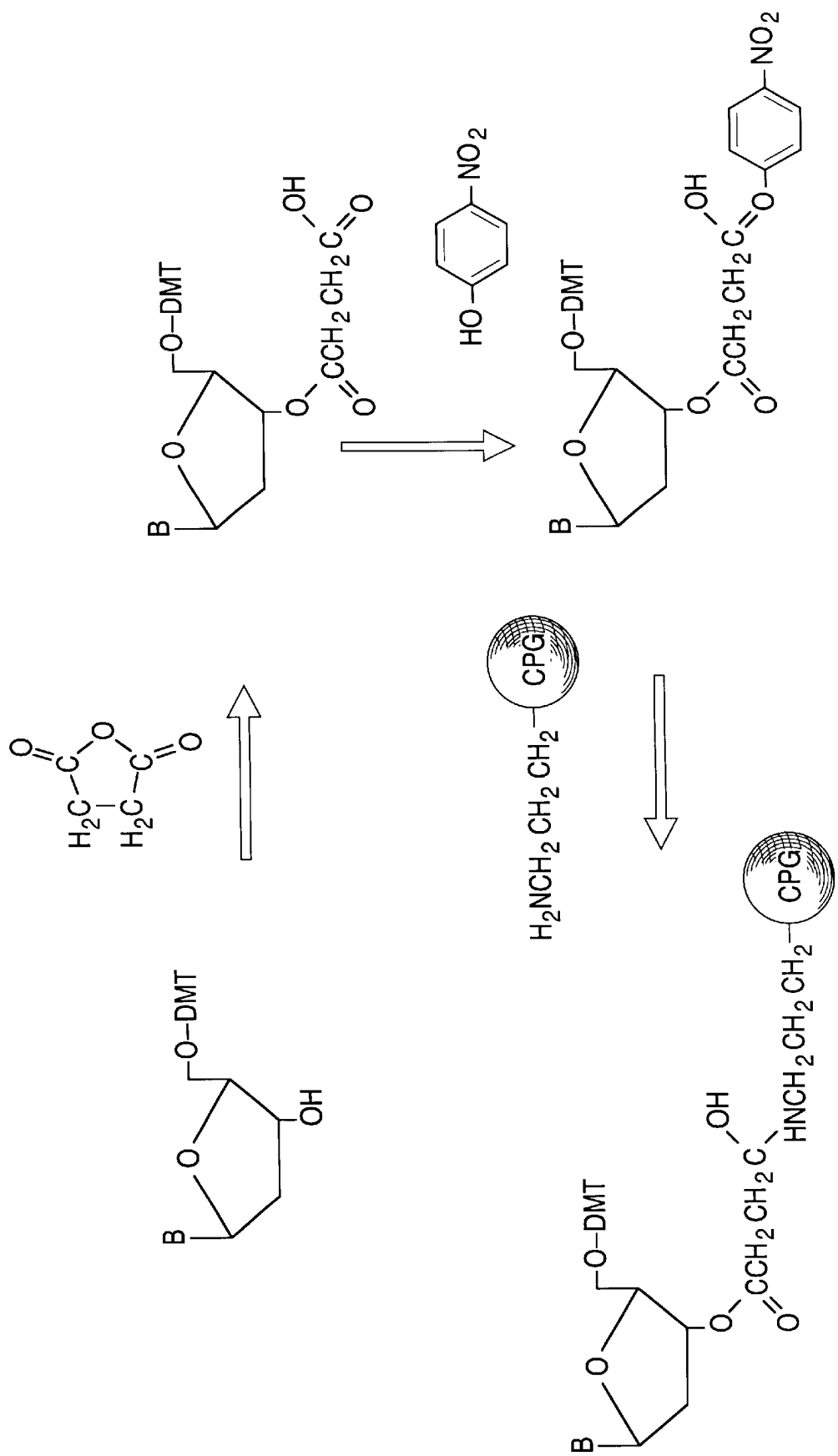

FIG. 10: Synthesis of carrier-bound L-deoxyribonucleosides (protected).

Figure 11:
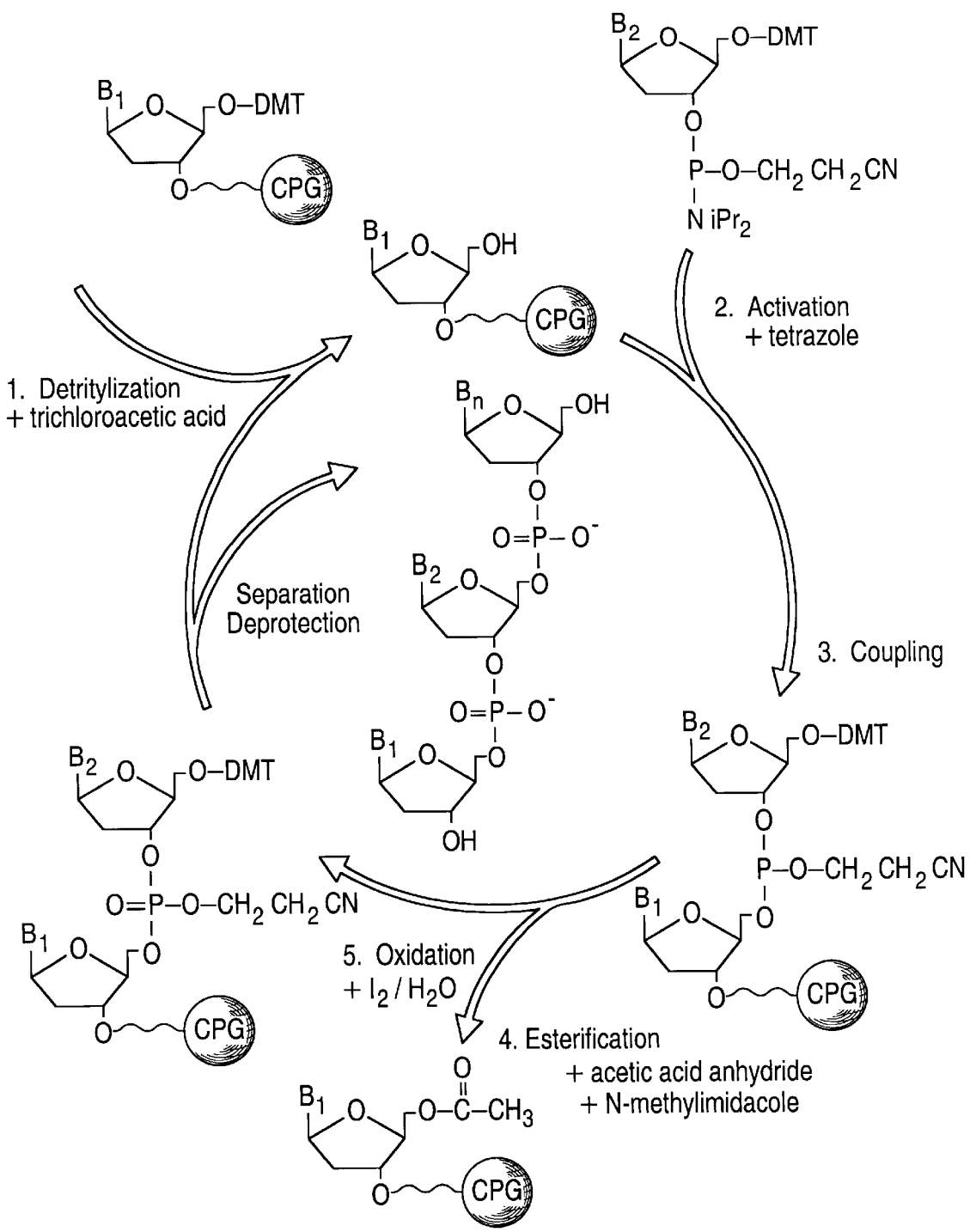

FIG. 11: Solid phase synthesis of L-DNA.

FIG. 12: Comparison of L-adenosine-binding sequences with consensus motif (SEQ ID NOS: 1–7). The framed nucleotides show areas of conserved sequences. W stands for A or T and H stands for A, C or T. The motif of box II could only be coordinated after comparing common secondary structures. Nucleotides from the area with original random sequences are represented by capital letters whereas nucleotides of the primer region are marked by small letters. Underlined positions take part in the base pairings in the secondary structural model. In order to insert the sequences D-A12 and D-A83 into the consensus diagram the 5'-terminals were arranged in the center of the scheme.

Figure 13:
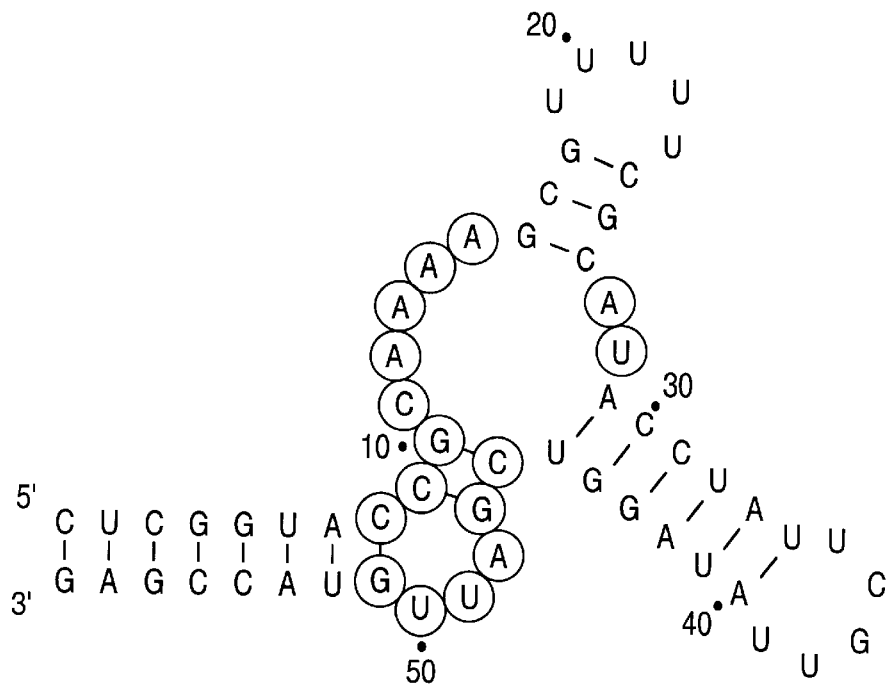

FIG. 13: Secondary structural model of D-A42d (SEQ ID NO:8). Conserved nucleotides are circled.

Figure 14:
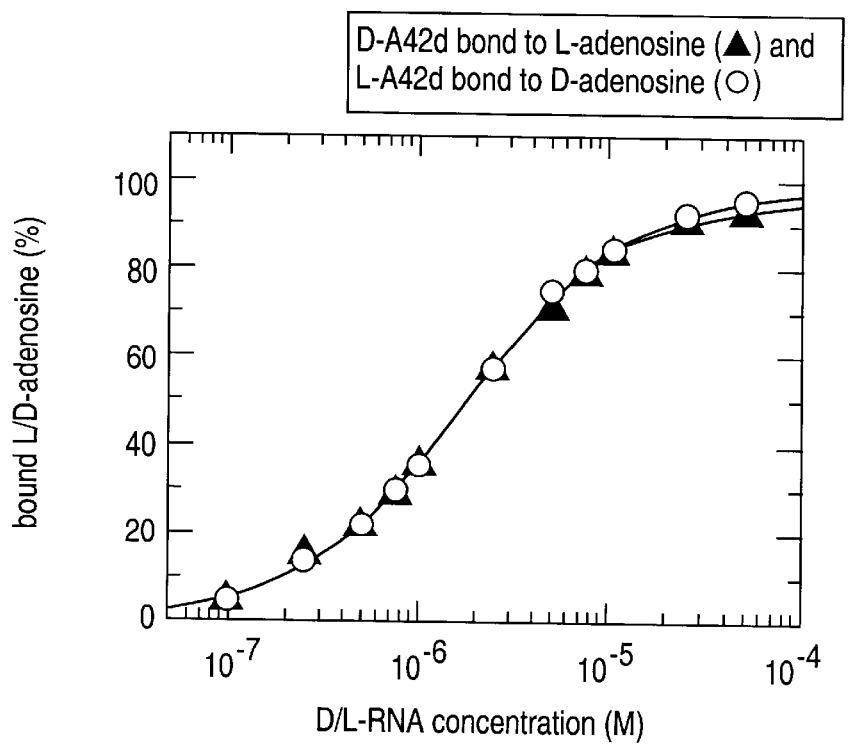

FIG. 14: D-A42d bond to L-adenosine (▲) and L-A42d bond to D-adenosine (○).

Figure 15:
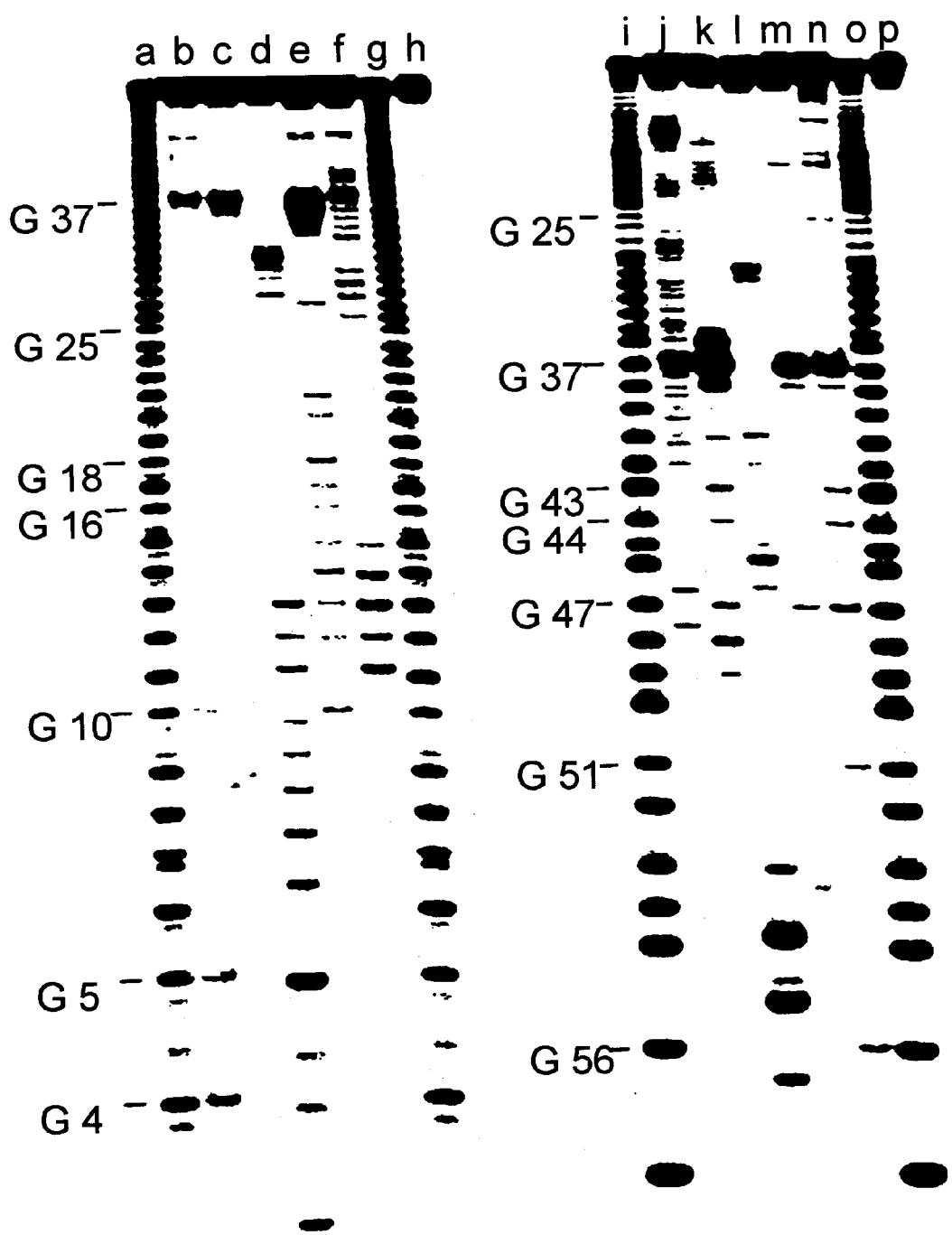

FIG. 15: Enzymatic digestion of D-A42d. 5'-labeled oligoribonucleotides were examined in the lanes a–h; 3'-labeled oligoribonucleotides were examined in the lanes i–p. Lanes a, g, i and o: alkali conductors; lanes b and n: RNase $T_1$ (denaturing conditions); lane c and m: RNase $T_1$; lanes d and l: RNase $V_1$; lanes e and k: RNase $T_2$; lanes f and j: nuclease $S_1$; lanes h and p: uncleaved.

Figure 16:
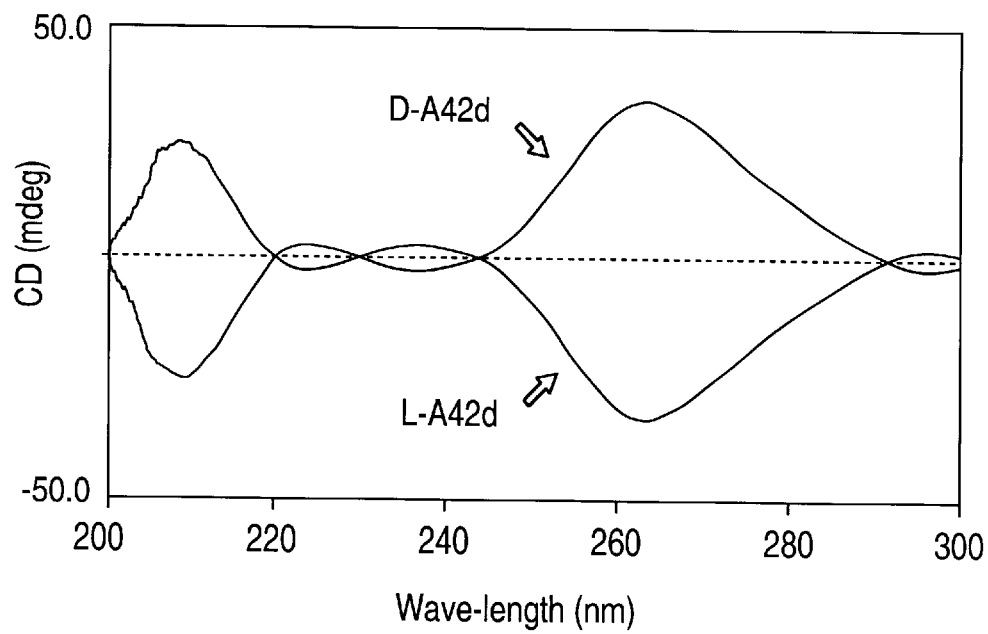

FIG. 16: CD spectra of D-A42d and L-A42d.

Figure 17:
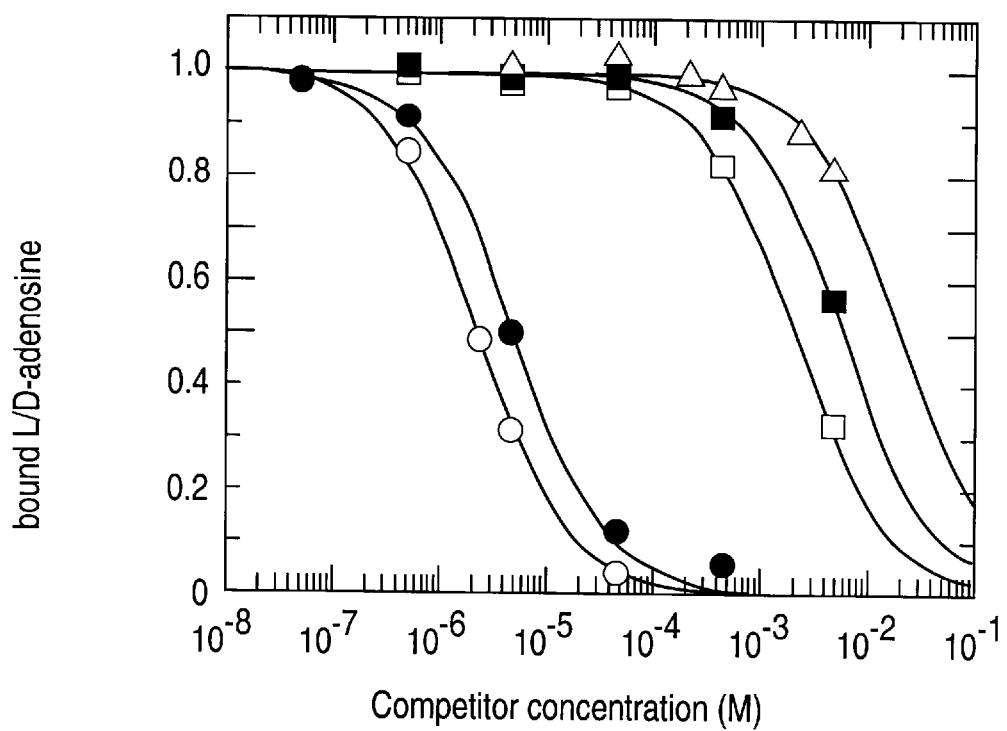

FIG. 17: Competitive binding curves of L-A42d. The competitions with D-adenosine (○), D-uridine (□), D-guanosine (●), D-cytidine (■), and L-adenosine (Δ) are shown. Each experiment was carried out twice.

FIG. 18: Competitive binding factors of L-A42d. The dissociation factors ($K_dc$) of nucleoside analogues and relative binding affinities ($K_dc/K_dD$-A) of competitors to D-adenosine competition ($K_dD$-A) are depicted.

Figure 19:
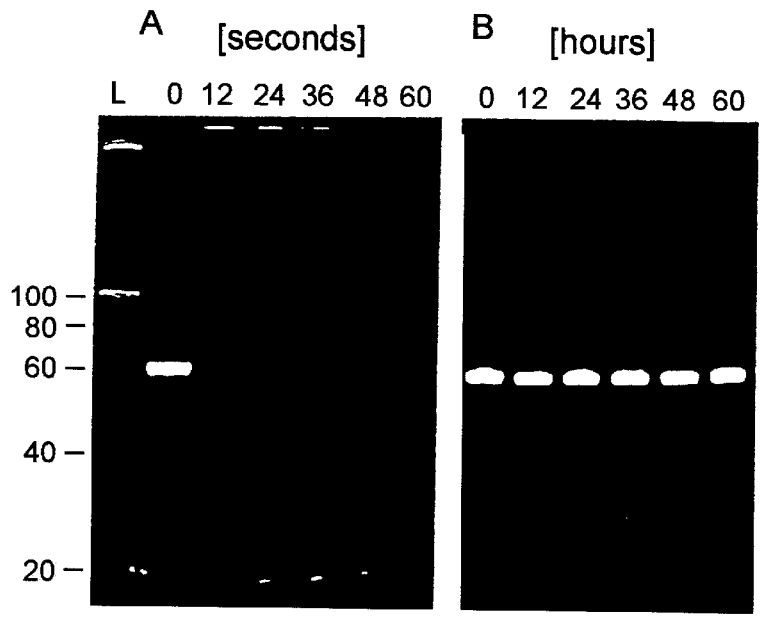

FIG. 19: Stability of oligonucleotide ligands in human serum. (A) D-oligoribonucleotide D-A42d and (B) L-oligoribonucleotide L-A42d. Aliquots were taken at indicated times. L marks the size standard (10 bp conductor). The results were reproduced in an independent experiment.

Figure 20:
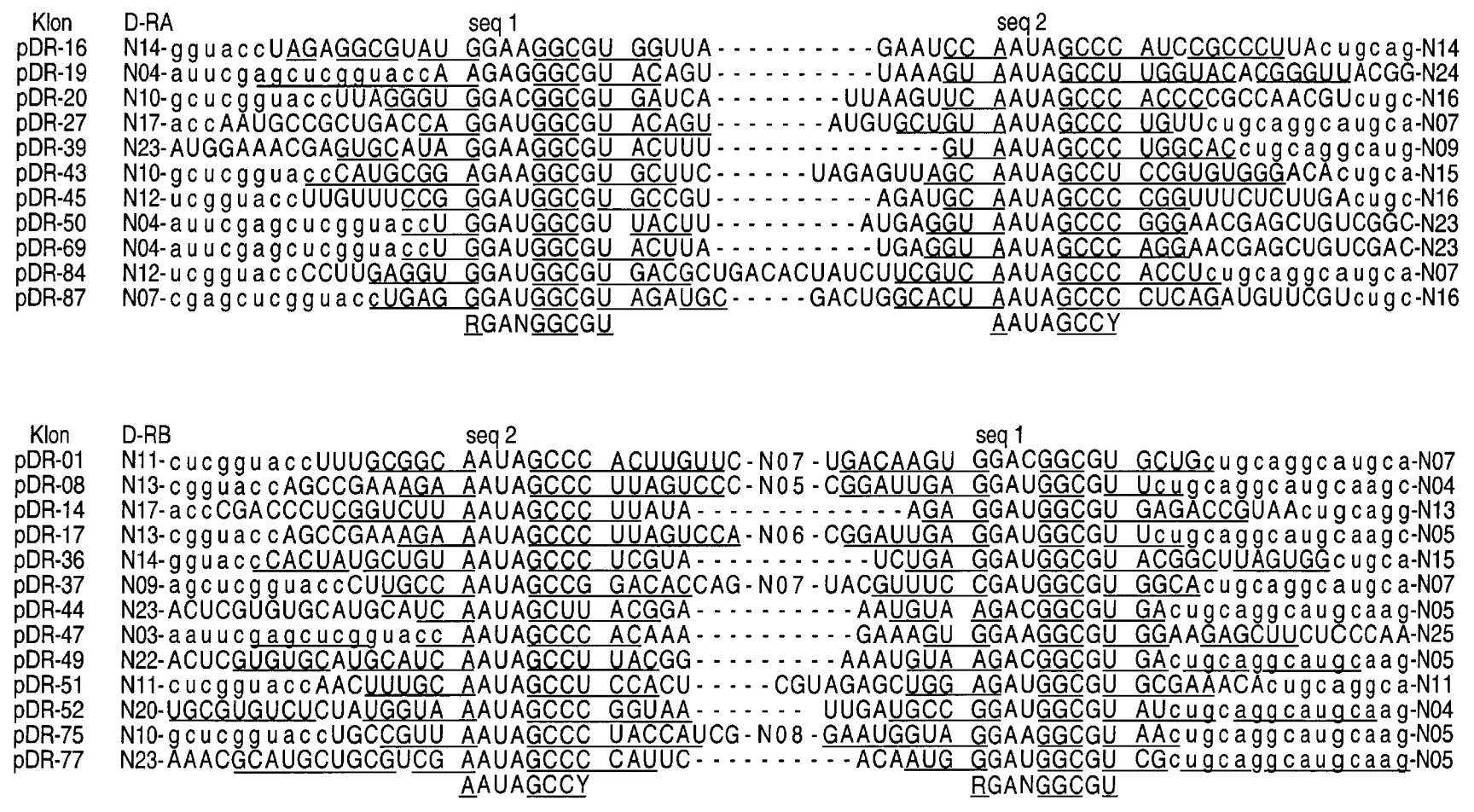

FIG. 20: Comparison of the D-arginine-binding sequences with consensus motif.

In the analysis, two classes of RNA molecules (referred to as D-RA (SEQ ID NOS:9–19) and D-RB (SEQ ID NOS:20–32)) were determined, each containing conserved sequence motifs (referred to as seq 1 and seq 2). Nucleotides of the region with originally random sequences are represented by capital letters, whereas nucleotides of the primer regions are marked by small letters. Underlined positions take part in base pairings in the secondary structural model.

Figure 21:
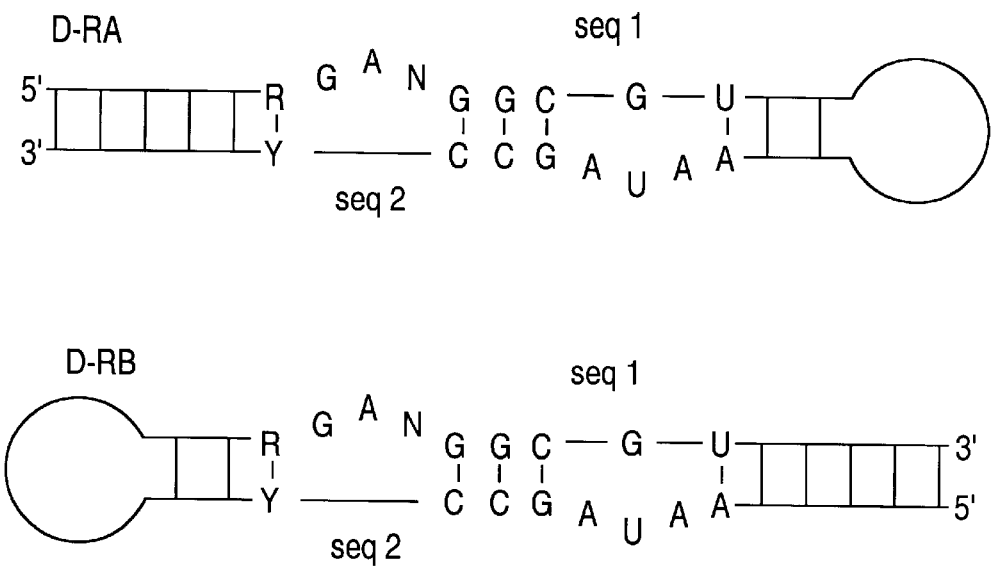

FIG. 21: Secondary structural model of the consensus motifs of D-RA (SEQ ID NO:33) and D-RB (SEQ ID NO:34).

Figure 22:
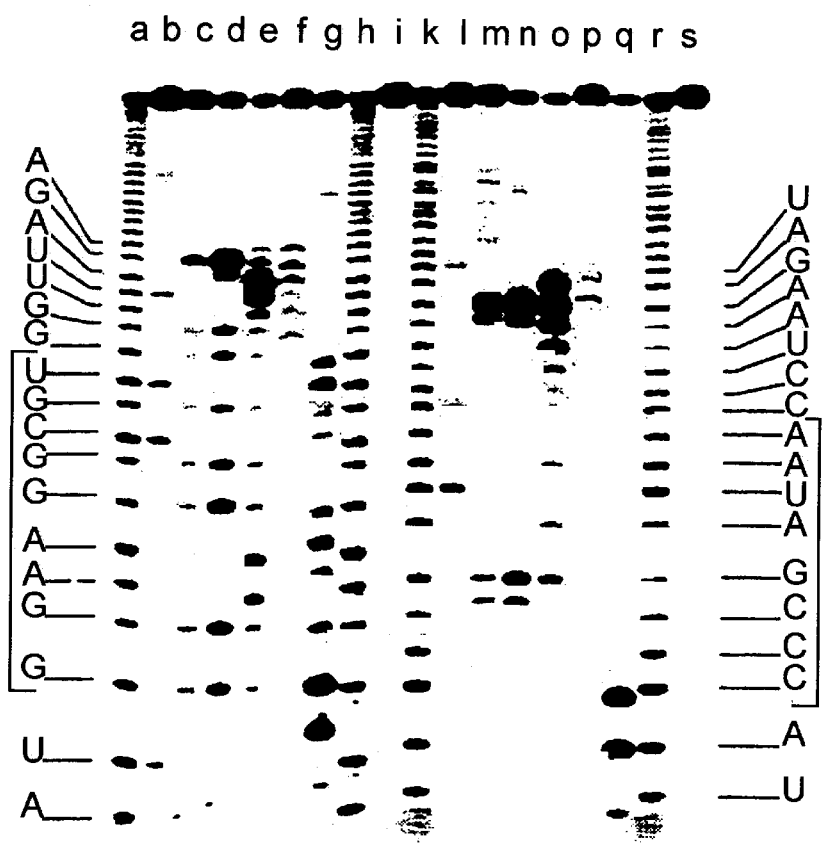

FIG. 22: Enzymatic digestion of D-R16c. The figure shows a autoradiogram of enzymatic digestion products analyzed on a denaturing polyacrylamide gel. The nucleotides in the conserved motifs are marked by brackets. 5'-labeled oligoribonucleotides were examined in the lanes a–i, 3'-labeled oligoribonucleotides were examined in the lanes k–s. Lanes a, h, k and r: alkali conductor; lanes d–g and n–q: native conditions. Lane d and n: RNase $T_1$. Lanes e and o: RNase $T_2$. Lanes f an p: RNase $S_1$. Lanes g and q: RNase $V_1$. Lanes b, c, l and m: denaturing conditions. Lane b and l: B. cereus. Lanes c and m: RNase $T_1$.

Figure 23:
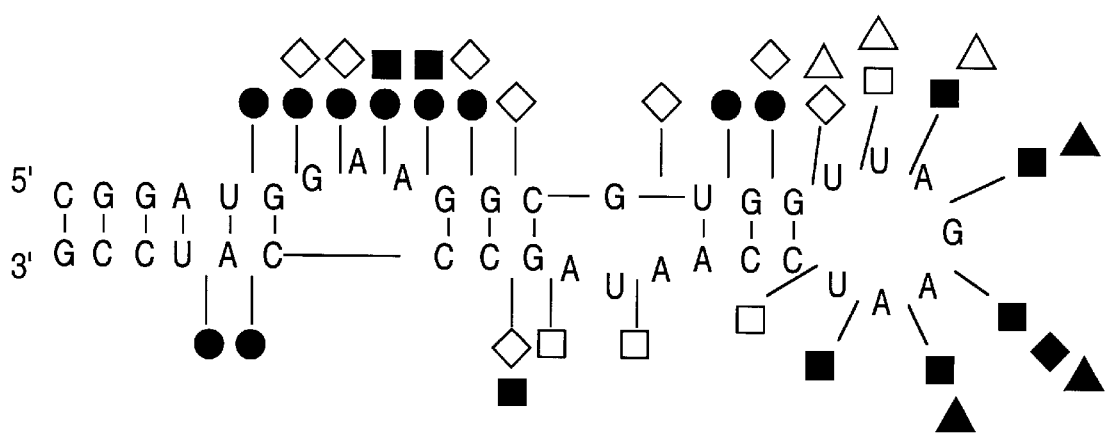

FIG. 23: Secondary structural model of D-R16c (SEQ ID NO: 35). The arrows mark the sites of RNase $T_1$ (◆), RNase $T_2$ (■), RNase $S_1$ ( ), and RNase $V_1$ (●). Filled-out symbols indicate strong cleavage, non-filled-out symbols indicate weak cleavage.

Figure 24:
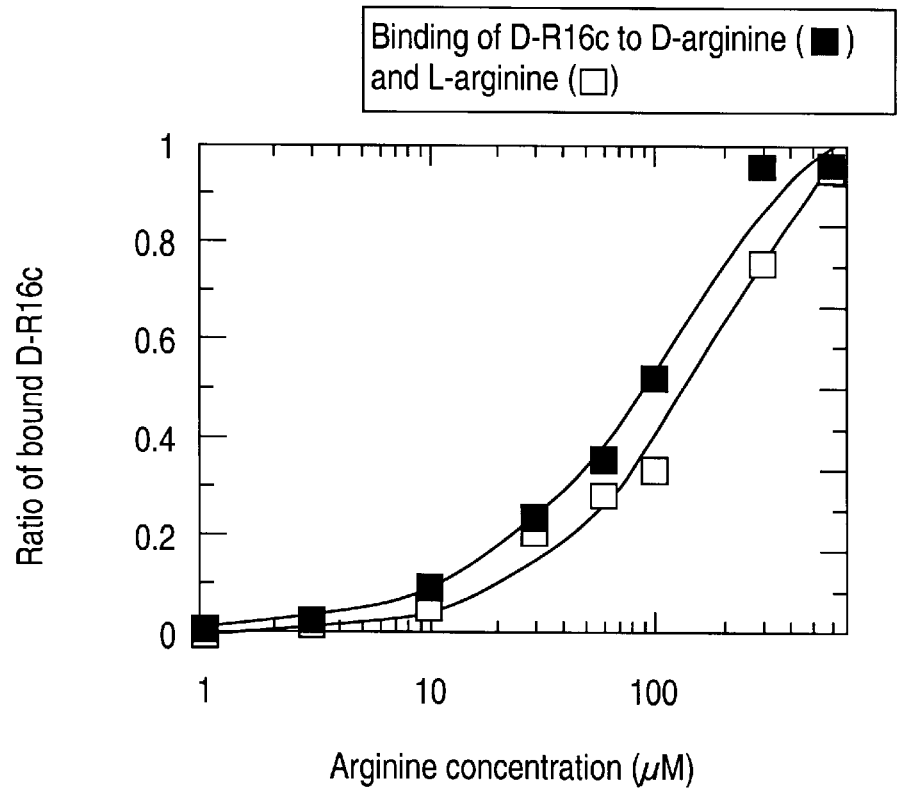

FIG. 24: Binding of D-R16c to D-arginine (■) and L-arginine (■).

Figure 25:
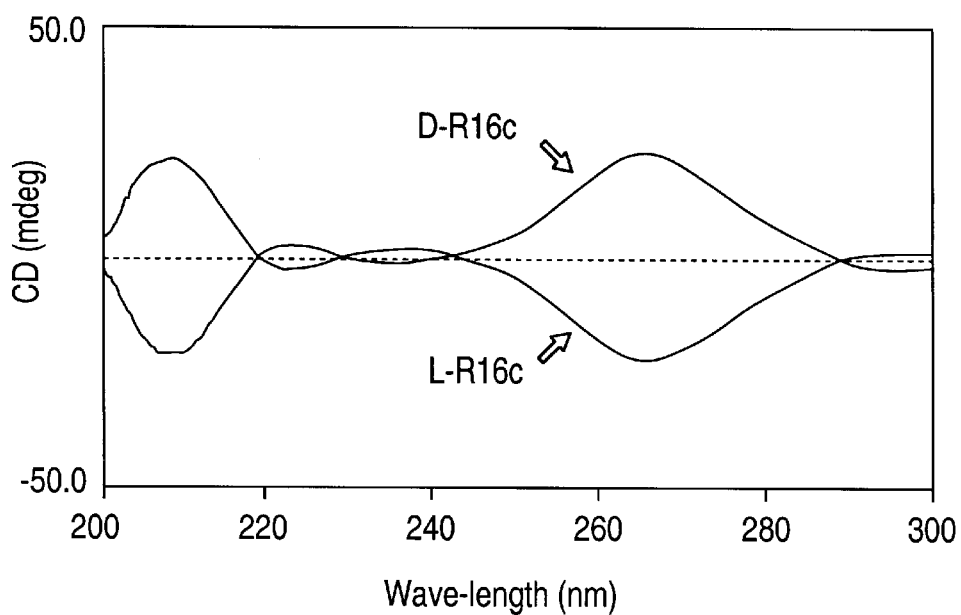

FIG. 25: CD spectra of D-R16c and L-R16c.

Figure 26:
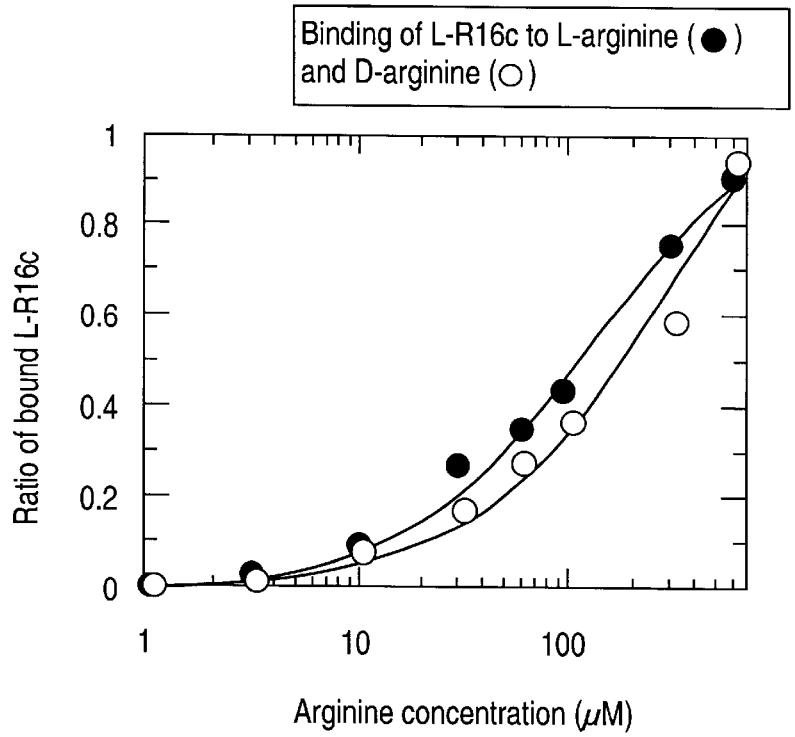

FIG. 26: Binding of L-R16c to L-arginine (●) and D-arginine (○).

Figure 27:
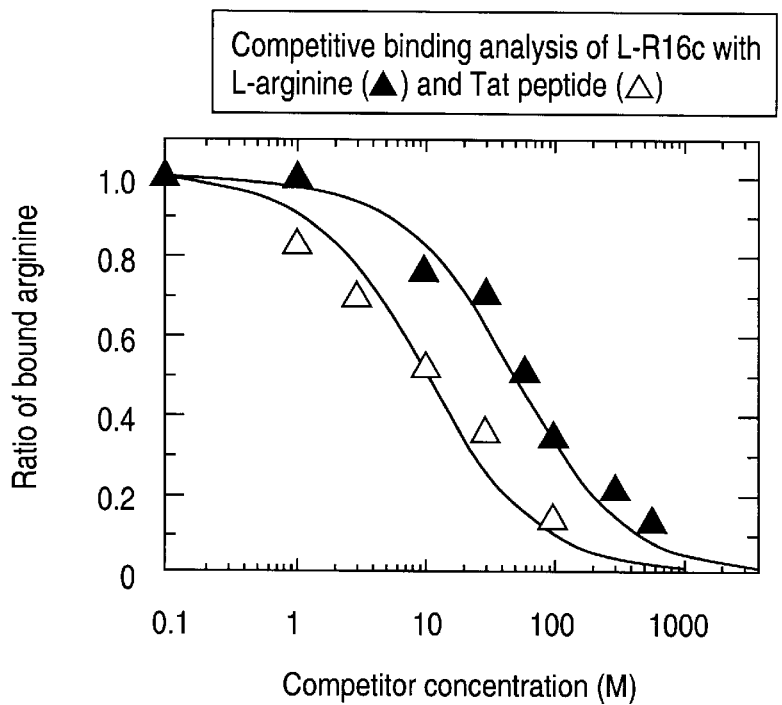

FIG. 27: Competitive binding analysis of L-R16c with L-arginine (▲) and Tat peptide (Δ).

Figure 28:
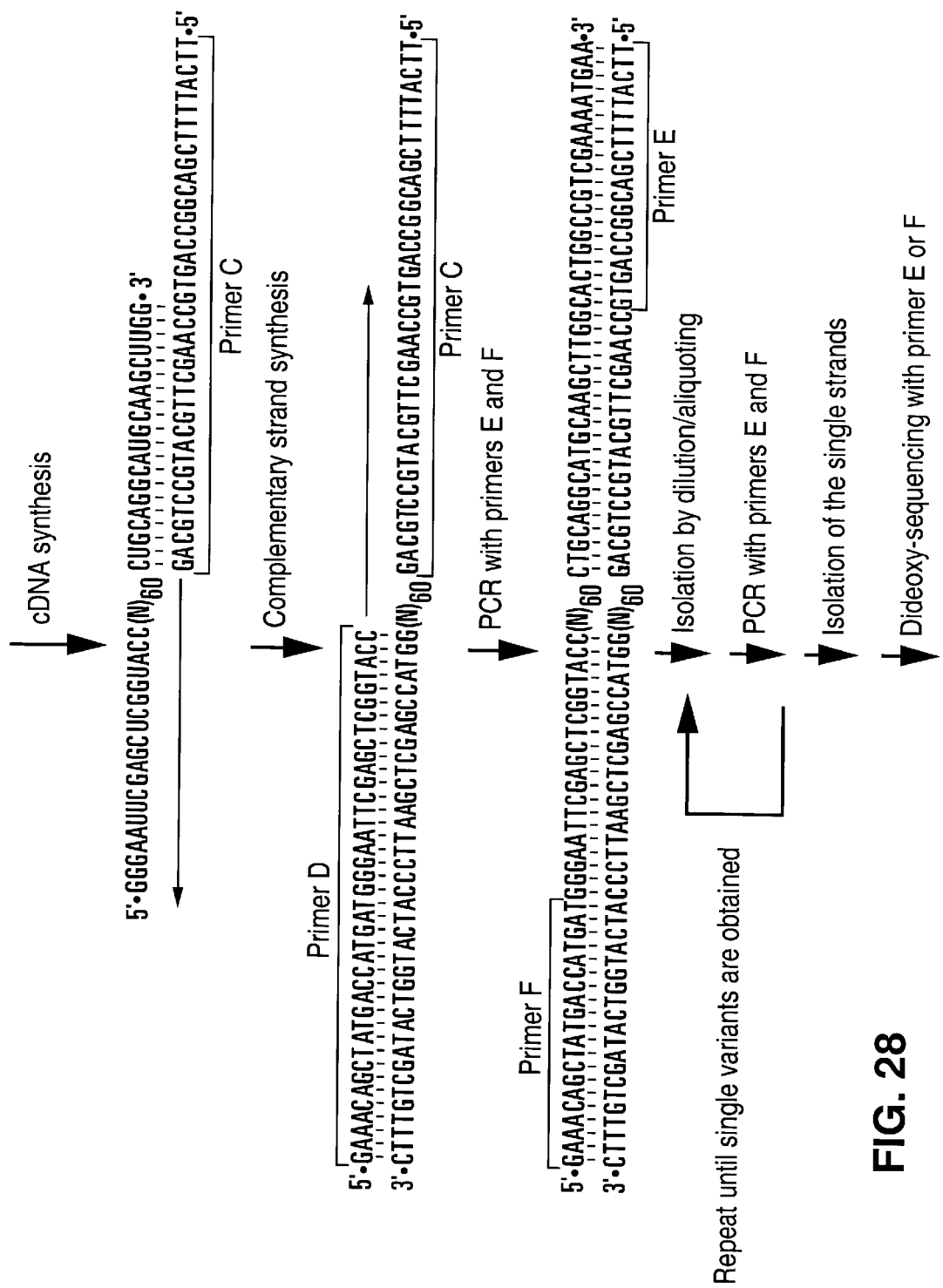

FIG. 28: Iterative in vitro isolation and sequencing. At first, the population of heterogeneous RNA molecules is translated into cDNA molecules by reverse transcriptase. After complementary strand synthesis the DNA molecules are amplified by PCR (SEQ ID NOS: 36–41). By diluting or aliquoting, the heterogeneity of the population may be reduced. After subsequent PCR-propagation, the method may be carried out in cycles until the DNA molecules are singled out. The sequence may then be determined by dideoxy-sequencing.

FIG. 29: Sequences determined after iterative in vitro isolation (SEQ ID NOS:42–44).

The examples illustrate the invention.

EXAMPLE 1

Synthesis of L-oligoribonucleotides

L-adenosine was prepared starting from L-arabinose according to Holý and Sorm (Collect. Czech. Chem. Commun. 34 (1969), 3383–3401) via benzyl-β-L-arabinopyranoside and transformation into 2-O-tosyl-5-O-trityl-L-arabinose. For the synthesis of L-uridine, at first the 2,2'-O-anhydro-L-uridine was depicted from L-arabinose according to Holý (Collect. Czech. Chem. Commun. 37 (1972), 4072–4087). Subsequently, it was benzoylated to the 3',5'-di-O-benzoyl-derivative according to Holý (Collect. Czech. Chem. Commun. 38 (1973), 423–427) and after a reaction with boron trifluoride etherate, the benzoylated L-uridine was subjected to alkali-blocking. L-cytidine and L-guanosine were obtained from the silylized heterocycles and from the peracylated pentose as described by Vorbrüggen et al. (Chem. Ber. 114 (1981), 1234–1255) for D-nucleosides, whereby the 2-N-acetyl-6-O-diphenylcarbamoylguanine was used for the synthesis of L-guanosine in analogy to Zou and Robins (Can. J. Chem. 65 (1987), 1436–1437). In order to depict peracylated pentose, the L-ribose was at first obtained from the L-arabinose by epimerization according to Abe et al. (Chem. Pharm. Bull. 28 (1980), 1324–1326) and subsequently derivatized to the 1-O-acetyl-2,3,5-tri-O-benzoyl-β-L-ribofuranoside in a three-stage synthesis, as described for D-isomers by Recondo and Rinderknecht (Helv. Chim. Acta 42 (1959), 1171–1173). In order to prepare the phosphoramidites for solid phase synthesis (FIG. 6), the exocyclic amino groups of the nucleosides were protected by benzoylation of adenosine and cytidine according to Ti et al. (J. Am. Chem. Soc. 104 (1982), 1316–1319) and isobutyrylation according to Flockerzi et al. (Liebigs Ann. Chem (1981), 1568–1585), as described for D-nucleosides. The base-protected nucleosides and uridine were transformed into their 5'-O-dimethoxytrityl-2'-O-triisopropylsilyl derivatives in analogy to Usman et al. (J. Am. Chem. Soc. 109 (1987), 7845–7854). The derivatives were then transformed into their respective 3'-O-(β-cyanoethyl-N,N-diisopropyl) phosphoramidites, according to Milecki et al. (Nucleosides Nucleotides 8 (1989), 463–474). Carrier-bound protected nucleosides were produced (FIG. 7) as described for the D-isomers by Usmann et al. (J. Am. Chem. Soc. 109 (1987), 7845–7854). For the chemical solid phase synthesis of the L-oligoribonucleotides, use was made of equipment of the company Applied Biosystems (model 391 PCR-MATE™ EP and model 394). The syntheses were carried out at a scale of 0,2 μmol by the DNA standard cycle (FIG. 8), whereby the coupling step was extended to 15 minutes. After synthesis, the carrier-bound, protected L-oligoribonucleotide was incubated in 1 ml of a 3:1 mixture of 32% ammonia and ethanol (v/v) for 24 hours at 55° C., in order to separate the oligonucleotide from the carrier and to cleave the protecting groups. The solution was taken off and the carrier material was washed with 400 μl of a 1:1 mixture of ethanol and water (v/v). A 5 μl aliquot was taken from the collected supernatants and UV absorption at 260 nm was determined. Subsequently, the sample was concentrated for drying. In order to cleave the 2'-hydroxyl-protecting group, the oligoribonucleotide was incubated in (10×$A_{260}$) μl tetrabutyl ammonium fluoride (1.1 M in tetrahydrofurane) and diluted (1×$A_{260}$) μl ethanol-water (1:1, v/v) and incubated for 72 h at RT. The superfluous tetrabutyl ammonium fluoride was removed by a tip 500 column (QIAGEN). Therefore, the sample was diluted to a total volume of 10 ml by means of 0.1 M triethyl ammonium acetate (TEAAc), pH 7.0 and put on the column equilibrated with 0.1 M TEAAc, pH 7.0. The column was washed twice with each 30 ml 0.1 M TEAAc, pH 7.0 and the sample was then eluted with 10 ml 2 M TEAAc, pH 7.0. The eluate was concentrated for drying and purified by denatured polyacrylamide gel electrophoreses. The product band was detected and excised by UV shadowing. The L-oligoribonucleotide was eluted from the gel piece with $H_2O$ for 10 hours and the eluate was desalted with an NAP™10 column (Pharmacia).

Synthesis of L-oligodeoxyribonucleotides

L-2'-deoxyadenosine and L-2'-deoxyguanosine were depicted by reduction, as described for D-nucleosides by Robins et al. (J. Am. Chem. Soc. 105 (1983), 4059–4065), starting from L-adenosine or L-guanosine. L-2'-deoxythymidine and L-2'-deoxycytidine were prepared in several stages according to Holý (Collect. Czech. Chem. Commun. 37 (1972), 4072–4087): the intermediate product 3',5'-di-O-benzoyl-2,2'-O-anhydro-L-uridine from L-uridine-synthesis was transferred into the 2'-chloro-2'-deoxy-derivative, which supplied L-2'-deoxyuridine after reduction and deblocking. The conversion into potassium hydroxide solution by means of formaldehyde and subsequent catalytic reduction supplied L-2'-deoxythymidine. L-2'-deoxycytidine was obtained from 3',5'-di-O-benzoyl-2'-deoxyuridine after transferring it into the 4-thio-derivative by conversion with methanol ammonia by means of pressure. The preparation of the phosphoramidite was carried out as described for D-deoxynucleosides (FIG. 9). In the case of L-2'-deoxyadenosine and L-2'-deoxycytidine the exocyclic amino groups were benzoylated according to Ti et al, loc. cit.; in the case of 2'-deoxyguanosine they were isobutyryliert. The 5'-hydroxyl group of the L-2'-deoxynucleosides was converted into the respective tritylethers by means of 4,4'-dimethoxytritylchloride according to Schaller et al. (J. Am. Chem. Soc. 85 (1963), 3821–3827). The L-2'-deoxynucleoside phosphoramidites were prepared according to Milecki et al, loc. cit., by converting the protected L-2'-deoxynucleosides with β-cyanoethyl-N,N,N',N'-tetraisopropyl phosphordiamidite. Carrier-bound, protected L-2'-deoxynucleosides were depicted in analogy to the D-isomers of Atkinson and Smith (in Gait (ed.), Oligonucleotide Synthesis, 1984, IRL Press, Oxford, p. 35–81) (FIG. 10). The solid phase synthesis of the L-oligodeoxyribonucleotides was carried out with equipment of Applied Biosystems (model 391 PCR-MATE™ EP and model 394) in 0.2 μmol DNA standard cycle (FIG. 11). After synthesis, the carrier-bound, protected L-oligoribonucleotide was incubated in 1 ml of 32% ammonia for 24 hours at 55° C. in order to separate the oligonucleotide from the carrier and the cleave the phosphate groups or base protecting groups. The solution was taken off and concentrated for drying. The taken-up L-oligodeoxyribonucleotide was purified by denaturing polyacrylamide gel electrophoresis. The product band was detected and excised by UV shadowing. The L-oligodesribonucleotide was eluted from the gel piece with $H_2O$ for 10 hours and the eluate was desalted with an NAP™10 column (Pharmacia).

EXAMPLE 2

Process of Identifying D-adenosine-specific L-oligoribonucleotides

Coupling of L-adenosine

In order to select the affine oligonucleotide-ligands by means of affinity chromatography, the L-adenosine was immobilized on Sepharose. The L-nucleoside was synthesized as described in Example 1 and alkylated to 1-carboxymethyl-L-adenosine in analogy to Jones and Robins (J. Am. Chem. Soc. 85 (1963), 193–201) with iodoacetic acid. After alkali transposition in 0.25 M NaOH for 2 hours at 95° C. the resulting $N^6$-carboxymethyl-L-adenosine was condensed with 1,6-diaminohexane to $N^6$-[(6-aminohexyl)-carbamoylmethyl]-L-adenosine in the presence of N-(3-dimethylaminopropyl)-N'-ethylcarbodiimide according to Lindberg and Mosbach (Eur. J. Biochem. 53 (1975), 481–486). The L-adenosine-derivative was coupled to a final concentration of 3.5 mM on CNBr-activated Sepharose 4B (Pharmacia).

Identification of an Adenosine Binding Motif

A combinatorial D-RNA library with about $10^{15}$ random sequences was obtained by means of in vitro transcription with T7-RNA-polymerase from a mixture of DNA molecules containing a region with random sequences with a length of 60 nucleotides. The region was limited by DNA areas having a length of 20 nucleotides and the following given sequence: (5'-CCA'AGC'TTG'CAT'GCC'TGC'AGN$_{60}$'GGT'ACC'GAG'CTC'GAA'TTC'CC-3') (SEQ ID NO:45). In order to avoid the enrichment of column-affine ligands, the RNA was first put on pre-columns with unloaded column material in all selecting cycles. In the first selecting cycle the ground column volume of the pre-column was 150 μl, that of the main column was 400 μl. About 4 nmol of Pool-RNA ($1.3 \times 10^{15}$ different molecules) were put on the columns in binding buffer (250 mM NaCl, 40 mM Tris/HCl pH 7.6, 5 mM $MgCl_2$ and 0.5 mM EDTA). During the first selecting cycle 0.06–0.07% of the used RNA could be specifically eluted from the affinity column with 15 mM L-adenosine in binding buffer. In all other selecting cycles, approximately 1 nmol RNA was applied and 100 μl-pre-columns or 250 μl main columns were used. In the sixth selecting cycle 38% of the bound RNA molecules could be specifically eluted with L-adenosine. This cycle was repeated in order to increase the stereo-specificity of the ligands. Before elution with L-adenosine the affinity material was washed with D-adenosine, whereby the part of the RNAs eluted with L-adenosine was reduced to 18%. After four further selection cycles the fraction of specifically bound RNA-ligands had again risen to 40%. The PCR products of this cycle were digested with the restriction endonucleases EcoRI and PstI, cloned into the vector plasmid pT7/T3 (Gibco BRL) and sequenced according to the method of Sanger. The sequence analysis of the selected RNA molecules resulted in a consensus motif which was found in 20% of the sequenced clones (FIG. 12). A common secondary structural model could be proposed for the sequences with consensus motif (FIG. 13).

Characterization of the L-adenosine-specific RNA Molecules

The individual dissociation factors ($K_d$) were determined by means of equilibrium dialysis in micro-dialysis-chambers. The two compartment were parted by means of a Spectra/Por® (Spectrum) cellulose ester dialysis membrane (limit for molecular weight: 2000). The RNA concentrations were determined in a spectral photometer at 260 nm. The individual extinction coefficients of the RNA molecules were determined according to A. J. Zaug et al. (Biochemistry 27 (1988), 8924–8931) by means of a complete alkali hydrolysis. In order to measure the dissociation factor the RNA was denatured in binding buffer for 10 minutes at 90° C., cooled to room temperature within 10 minutes and then equilibrated in binding buffer with concentrations of 0.1 to 50 μM against a solution of 10 nM D-[2,8-$^3$H]adenosine (Moravek Biochemicals, Inc.) or L-[2,8(n)-$^3$H]adenosine (tritiated by Amersham). Each compartment was filled with 40 μl solution. After incubating for 24 h at 18° C. 35 μl aliquots were taken off and the radioactivity of the samples was measured in a scintillation counter. The difference in radioactivity in the two compartments relative to the radioactivity in the RNA-containing compartment was assumed to be the adenosine-bond to RNA in percent. The data were adapted to a standard binding equation for 1:1 stoichiometry by means of non-linear regression analysis according to Connors (Binding constants, 1987, John Wiley & Sons, New York). The T7 transcripts of the clones with consensus motif showed dissociation factors ranging between 1.1 and 10 μM for the bond of L-adenosine. Shortened versions of the best ligand D-A42 ($K_d$ of 1.1±0.1 μM) were examined. The 58-mer D-A42d (FIG. 13) showed a dissociation factor of 1.7±0.1 μM (FIG. 14). Apart from the shortenings at the 5'- and 3'-ends, D-A42d lacks two G nucleotides between position 31/32 and 41/42. In addition, C was substituted for A in position 54. The secondary structural model of D-A42d is in accordance with the data obtained from the nuclease digestion (FIG. 15). For the native digestion the 5'- and 3'-labeled oligoribonucleotides were denatured at 90° C. and hybridized in binding buffer. For each cleaving reaction 100,000 cpm (≈30 fmol) of marked oligoribonucleotide was used. The cleavages were carried out as described by G. Knapp (Methods Enzymol. 180 (1989), 192–212). The cleavage products were separated on denaturing 25% polyacrylamide gels. The only G in the predicted single stranded region at position 37 was clearly cleaved by RNase $T_1$. The cleavages of RNase $T_2$ at positions G47 and A48 and the single strand-specific nuclease $S_1$ at positions G10, C11, A12, A13 and A27 confirmed the conserved internal loops between G10/G16 and G47/G51, as well as the loop region between U34/A40. The cleavages with the double strand-specific RNase $V_1$ at positions U2-A7, G10, C30-U32, U45 and U52-G56 are in accordance with the secondary structural model. The reactivity of single strand- and double strand-specific nucleases in the predicted hairpin region between positions G16/C26 was low; it may thus be assumed that a compact tertiary structure occurs.

Reciprocal Binding Specificities

After identifying D-A42d an L-oligoribonucleotide with an identical nucleotide sequence (FIG. 13) was prepared by chemical solid phase synthesis, as described in example 1. The stereochemical purity of the L-oligoribonucleitde was evaluated by circular-dichroism-spectrometry. CD spectra were taken up by one $A_{260}$ oligonucleotide in 0.1 M NaCl and 10 mM sodium phosphate, pH 7.0 at 4° C. with a JASCO J-600 spectropolarimeter. The spectra of D-A42d and L-A42d show opposite optical reactions of similar size (FIG. 16). When compared to the binding of D-A42d to L-adenosine, the mirror-symmetrical ligand L-A42d showed an identical affinity for D-adenosine ($K_d$ of 1.8±0.1 $\mu$M) (FIG. 14). The proof of the chiral binding specificities could be confirmed by competition. The affinities of D-A42d for D-adenosine and L-A42d for L-adenosine are at >20 mM (FIGS. 17 and 18). Thus, the homochiral interactions are more than 9000 times weaker than the heterochiral affinities. The reciprocal chiral properties of the ligands show that the parity of the nucleic acids is not damaged and that the binding activities are exclusively determined by the nucleotide sequence.

Molecular Component of the Interaction with L-A42d

The interaction of L-oligoribonucleotide and D-adenosine was characterized by competition with nucleoside analogues (FIGS. 17 and 18). The competition experiments were determined by equilibrium dialysis in micro dialysis chambers, as described above, whereby 3 $\mu$M RNA was equilibrated with 240 nM adenosine and increasing concentrations with competitor. The percentage of bound adenosine was determined as described above and normalized to 1 in the absence of competitor. The data were adapted to a standard competition equation with 1:1 stoichiometry of competitor to RNA according to Lin and Riggs (loc. cit.), whereby the dissociation factor of 1.8 $\mu$M for used for the L-A42d bond to D-adenosine. The N-glycosidic bond of the nucleoside has an important function in the interaction since D-guanosine exhibits a $K_dc$ of 4.8 $\mu$M, whereas the competitor dissociation factors of D-uridine and D-cytidine are within the milimolar range. In the absence of the 2'-hydroxyl group the $K_dc$ is increased to 1.4 mM for 2'-deoxy-D-adenosine and to 12.9 mM for 2'-O-methyl-D-adenosine, whereas the competition with 3'-deoxy-D-adenosin and 3'-O-methyl-D-adenosine leads to a similar or even better $K_dc$ as was obtained for D-adenosine. Thus, apart from the N-glycosidic bond, the 2'-hydroxyl group also seems to be important for the molecular interaction.

Serum Stability of the Adenosine-specific Ligands

The D- and L-oligoribonucleotides were incubated in a concentration of 10 $\mu$M in 90% human serum (Sigma, H-1388) which was buffered with 10 mM sodium phosphate, pH 7.0. In order to obtain constant volumes and pH conditions in long-term experiments, the long-term experiments were carried out in an incubator at 37° C., 94.5% humidity and 5% $CO_2$. The aliquots taken were mixed with like volumina of a stop solution (8 M urea, 50 mM EDTA and 2% SDS) and frozen in liquid nitrogen. The samples (55 pmol RNA) were separated on a denaturing 12% polyacrylamide gel. The gels were stained with ethidium bromide solution (1 $\mu$g/ml) and the bands were rendered visible at 254 nm. Digitalized gel recordings by means of a video-densitometer were evaluated by a computer program. Whereas the D-oligoribonucleotide D-A42d is degraded in human serum within a few seconds, no degradation may be determined for the L-oligoribonucleitde L-A42d under identical conditions, even after 60 hours (FIG. 19).

EXAMPLE 3

Method for the Identification of L-arginine-specific L-oligoribonucleotides

Coupling of D-arginine

The affinity material was prepared by coupling of D-arginine to epoxy-activated agarose. Therefore, 5 g epoxy-activated agarose 6B (Pharmacia) was washed with water and coupling buffer (0.1 M sodium carbonate buffer, pH 9.5). The agarose was resuspended in 10 mM D-arginine (Sigma) in coupling buffer and traces of L-[4,5-$^3$H]arginine. After incubation for 24 hours at room temperature and by slightly shaking it, the material was washed with coupling buffer and water. The agarose was then incubated in 1 M ethanolamine, pH 10.0, for 4 hours at 32° C. in order to block remaining active groups. The capacity of the gel was determined by scintillation counting. Except for the coupling step, the pre-column material was prepared in an identical manner.

Identification of a D-arginine Binding Motif

A combinatorial D-RNA library with $10^{14}$ random sequences was obtained by in vitro transcription by T7-RNA polymerase from a mixture of DNA molecules containing a region of random sequences with a length of 50 nucleotides. The region was limited by DNA areas with given sequences and a length of 20 nucleotides (cf. Example 2). Eleven selection cycles were carried out as described in Example 2, whereby the affinity material was loaded with 1 mM D-arginine and a solution of 320 mM NaCl, 50 mM Tris-HCl, pH 7.5, and 5 mM $MgCl_2$ was used as selection buffer for chromatography. RNA variants with an affinity for the column material were removed in all cycles by binding to the agarose pre-column material. D-arginine specific RNA molecules were eluted with 4 column volumes of a 15 mM D-arginine solution in selection buffer. In order to increase the stereo-selectivity of the ligands, the affinity column was, after the fifth cycle, first washed with L-arginine and only then the still-bound RNA molecules were eluted with D-arginine. After eleven selection cycles the RNA molecules were reversely transcribed, cloned and sequenced.

During sequencing of 55 clones 41 different sequences could be found. The sequence comparison (FIG. 20) resulted in two highly conserved sequence elements present in almost 60% of the sequences: a motif with a length of 9 nucleotides (seq1) and a motif with a length of 8 nucleotides (seq2). In 11 sequences, seq1 was nearer to the 5'-terminal than seq2, whereas in 13 sequences the consensus motifs were present in reverse order. The sequences with the consensus motifs could be folded-up into a common secondary structural model with the algorithm of Zuker (loc. cit.) (FIG. 21). Starting from this model, shortened variants from D-R16 were prepared by means of chemical RNA synthesis. The variant D-R16c, an RNA molecule with a length of 38 nucleotides (FIG. 23), contains the essential structural elements for the specific binding of D-arginine (see below).

Characterization of the L-arginine-specific RNA Molecules

The structural analysis of D-R16c by enzymatic digestion with the nucleases T1, T2, S1 and V1 (FIG. 22) is in accordance with the secondary structural model (FIG. 23). The phosphor diester bonds in the hairpin loop and the internal loops could be cleaved by means of single strand-specific nucleases. Whereas the nucleotides are highly conserved within the internal AUA loop and in the GAN bulge, no conserved positions could be found for the nucleotides in the hairpin structure connecting seq1 and seq2. Therefore, the hairpin region does not seem to be directly involved in the binding of arginine.

Reciprocal Binding Specificities

The L-enantiomers of D-R16c (named L-R16c) was obtained by means of chemical solid phase synthesis (cf. example 1). When characterizing D-R16c and L-R16c in circular dichroism spectrometry mirror-symmetrical spectra were obtained (FIG. 25, cf. example 2), as was expected. The affinity of the oligonucleotide-ligands for D- or L-arginine were determined by equilibrium dialysis in micro-dialysis-chambers, as described in example 2. Increasing amounts of L-[4,5-$^3$H]arginine (ICN) or D-[2,3-$^3$H]arginine (DuPont, NEN, client synthesis) were equilibrated in binding buffer (50 mM NaCl, 50 mM Tris-HCl, pH 7.5, 5 mM MgCl$_2$) with 10 $\mu$M of the D- or L-RNA. D-R16c showed a coefficient ($K_d$) of 135±25 $\mu$M for the interaction with D-arginine (FIG. 24). L-R16c was able to bind L-arginine with an undiscernable $K_d$ of 129±18 $\mu$M (FIG. 26). The binding of D-R16c to D-arginine took place stereo-selectively with a preference of D-arginine which was 1.7 times as high as that of L-arginine (FIG. 24). L-R16c showed a 1.8 times higher stereo-selectivity for L-arginine (FIG. 26). These results emphasize the reciprocally identical binding properties of the oligonucleotide enantiomers.

Molecular Components of the Interaction with L-R16c

In order to characterize the specific components involved in the binding, competitive binding experiments were carried out (cf. Example 2). Increasing amounts of competitor were added to 10 $\mu$M L-[4,5-$^3$H]arginine and equilibrated against 10 $\mu$M L-R16c. The share of bound L-arginine was determined from the ratio of bound arginine with competitor to bound arginine without competitor. The data were adapted to a standard binding equation according to Lin and Riggs (loc. cit.), whereby a $K_d$ of 130 $\mu$M was used for the binding of L-R16c to L-arginine. A competitive dissociation factor ($K_dc$) of 60±10 $\mu$M was determined for L-R16c by means of L-arginine as competitor. The binding affinity of L-R16c for L-lysine ($K_dc$=270±50 $\mu$M) was about 40 times as high as for D-lysine ($K_dc$>10 mM). The result indicated that the α-carboxyl group takes part in the binding. Agmatin, an arginine analogue lacking the α-carboxyl group, showed a competitive dissociation factor of 270±70 $\mu$M. This result indicates that the L-RNA also interacts with the guanidinium-lateral-chain. The simultaneous binding of the lateral chain and the α-carboxyl group leads to the L-preference of the binding region. The relatively strong binding to the lateral chain explains the low stereo-selectivity of L-R16c for L-arginine.

Binding of L-R16c to an HIV-Tat-peptide

The arginine-specific binding properties of L-R16c were used in order to test the interaction with peptides. Competitive binding experiments were carried out with a peptide carrying the sequence YGRKKRRQRRRP (SEQ ID NO:46) from the HIV-Tat-protein. Deviating from the above-described competition analyses, a dialysis membrane with a molecular weight limit of 8000 was used. The affinity of L-R16c for the Tat-peptide ($K_dc$=26±5 $\mu$M) was twice as high as the affinity for L-arginine (FIG. 27).

Serum Stability of the Arginine-specific Ligands

The stability of D-R16c and L-R16c was examined in human serum, as described in Example 2. Whereas D-R16c could no longer be proven after less than a minute, no degradation of L-R16c could be stated, even after incubation for 60 hours at 37° C.

EXAMPLE 4

Method for Iterative In vitro Isolation and Sequencing

The RNA molecules of the tenth selecting cycle described in Example 2 were again transferred into the complementary cDNA by means of reverse transcriptase. Subsequently, opposite strand synthesis and finally PCR amplification were carried out (FIG. 28). Deviating from Example 2, oligonucleotides were used as primers which exceed the RNA- or DNA-matrix by 20 nucleotides each (primer C and D, FIG. 28). This extension of the PCR products was carried out in order to to completely determine the randomized region by dideoxy-sequencing. The PCR products were purified by means of a denatured polyacrylamide gel (7 M urea). The DNA molecules were eluted from the gel with water and desalted in gel filtration. The isolated amount of DNA products was determined by absorption at 260 nm. For iterative isolation, the DNA molecules were diluted in several steps in such a way that theoretically a number of about 100 molecules was reached. From this degree of dilution, a further reduction of the number of DNA molecules could be achieved by aliquoting. The few remaining DNA molecules present in an aliquot were propagated by means of PCR (primer E and F, FIG. 28). Several PCR reactions were necessary for each cycle in order to amplify the DNA molecules in such a way that they could be proved on a polyacrylamide gel (5 pmol). After each PCR reaction, the obtained material was purified by ethanol precipitation in the presence of glycogen. In order to isolate single strands primers were used in every new PCR reaction which were phosphorylated at the 5'-end (primer E or F, FIG. 28). The 5'-phosphate group was introduced during solid phase synthesis of the primers. Before the actual sequencing reactions took place, single stranded DNA was produced from double stranded PCR products by selectively degrading the phosphorylated strand by lambda exonuclease (Higuchi and Ochman, Nucleic Acids Res. 17 (1989), 5865). The sequencing was then carried out according to the conventional dideoxynucleotide technique (Sanger et al., Proc. Natl. Acad. Sci. USA 74 (1977), 5463–5467). If the evaluation of the sequence gels made evident that more variants were present, the dilution process was repeated until it was possible to determine the individual sequence. By means of this method three new variants could be identified (FIG. 29) apart from the already known variants (FIG. 12).

What is claimed is:

1. Method of producing L-nucleic acids binding to a target molecule having natural configuration, said method comprising the following steps:
   (a) producing a heterogeneous population of D-nucleic acids;
   (b) bringing the population of step (a) into contact with a racemic mixture of the target molecule;
   (c) separating the D-nucleic acids not binding to the racemic mixture of the target molecule;
   (d) sequencing the D-nucleic acids binding to the racemic mixture of the target molecule; and
   (e) producing L-nucleic acids, the sequence of which is identical to the sequences of the D-nucleic acids determined in step (d).

2. The method of claim 1, wherein a D-nucleic acid of step (d) binds to an optical antipode of the target molecule present in the racemic mixture.

3. The method of claim 1, wherein the following step is added after step (c):
   (ca) amplifying the D-nucleic acid binding to the racemic mixture of the target molecule thereby producing amplified D-nucleic acids.

4. The method of claim 3, wherein the D-nucleic acids of the population of step (a) exhibit at their 5'- and 3'-ends primer binding sites or complementary sequences to primer binding sites which allow for an amplification of the D-nucleic acids obtained in step (ca) by PCR.

5. The method of claim 3, wherein the D-nucleic acid of the population of step (a) exhibit at their 5'- and 3'-ends binding sites or complementary sequences to the binding sites for a DNA-dependent RNA-polymerase, which allow for the in vitro transcription of the amplified D-nucleic acids obtained in step (ca).

6. The method of claim 3, wherein during amplification nucleotides are incorporated into nucleotide strands to be newly synthesized which are not present in the D-nucleic acids present in step (a) which binds to the target molecule.

7. The method of claim 3, wherein the following step is added after step (ca):
   (cb) bringing the amplified D-nucleic acids into contact with the racemic mixture or an optical antipode of the target molecule, followed by steps (b) but before carrying out step (d), wherein the steps (cb), and (b) may be repeated in this order one or more times.

8. Method of producing L-nucleic acids comprising the following steps:
   (a) producing a heterogeneous population of L-nucleic acids;
   (b) bringing the population of step (a) into contact with a target molecule;
   (c) separating the L-nucleic acids not binding to the target molecule;
   (d) sequencing the L-nucleic acids binding to the target molecule;
   (e) producing L-nucleic acids, the sequence of which is identical to the sequences determined in step (d).

9. The method of claim 8, wherein the following step is additionally inserted after step (c):
   (ca) amplifying the L-nucleic acids binding to the target molecule.

10. The method of claim 9, wherein the L-nucleic acids of the population of step (a) exhibit at their 5'- and 3' ends primer binding sites or complementary sequences to primer binding sites which allow for an amplification of the L-nucleic acids obtained in step (ca) by mirror-symmetrical PCR.

11. The method of claim 9, wherein during amplification nucleotides are incorporated into the nucleotide strands to be newly synthesized, that are not present in the L-nucleic acids present in step (a), which binds to the target molecule.

12. The method of claim 9, wherein the following step is added after step (ca):
   (cb) bringing the amplified L-nucleic acids into contact with the target molecule, which is followed by step (b) and possibly (ca) before carrying out step (d), wherein the steps (cb), (b) and possibly (ca) may be repeated in this order once or several times.

13. The method of claim 1, or 8 wherein the interaction consists in a binding.

14. The method of claim 1 or 8, wherein the binding consists in a catalytic reaction.

15. The method of claim 1 or 8, wherein the nucleic acids are deoxyribonucleic acids.

16. The method of claim 1 or 8, wherein the nucleic acids are ribonucleic acids.

17. The method of claim 16, wherein the ribonucleic acids are ribozymes.

18. The method of claims 1 or 8, wherein the target molecule is a amino acid, a peptide, a polypeptide or a protein consisting of several polypeptides.

19. The method of claim 1 or 8, wherein the target molecule is a single stranded RNA, a double stranded RNA, a single stranded DNA or a double stranded DNA or a combination of thereof.

20. The method of claim 1 or 8, wherein the target molecule is an antibiotic or another pharmaceutically active substrate or a pre-stage thereof.

21. The method of claim 1 or 8, wherein the target molecule is a sugar molecule.

22. The method of claim 1 or 8, wherein the production of the L-nucleic acids of step (e) takes place chemically or enzymatically.

23. The method of claim 22, wherein the chemical production comprises the following steps:
   (ea) synthesis of L-nucleotides;
   (eb) synthesis of protected L-nucleoside phosphoramidites; and
   (ec) solid phase synthesis of L-nucleic acids by means of a synthesizer.

24. The isolated L-nucleic acid specifically interacting with a target molecule defined in claim 1 or 8, which is a ribozyme.

25. A composition comprising an isolated D-nucleic acid obtained according to the method of claim 1, in step (c) further comprising a matrix used for producing an L-nucleic acid with an identical nucleic acid sequence.

26. The method of claim 1, wherein the following steps are added after step (b):
   (ca) amplifying the D-nucleic acid binding to the optical antipode of the target molecule thereby producing amplified cDNAs; and
   (cb) bringing the amplified D-nucleic acids into contact with the optical antipode of the target molecule, followed by steps (b) but before carrying out step (d), wherein the steps (cb), and (b) may be repeated in this order one or more times.

27. The method of claim 15, wherein the nucleic acids are deoxyribozymes.

28. The method of claim 1, wherein an L-adenosine used for producing L-nucleic acids of step (e) is prepared via benzyl β-L-arabinopyranoside and 2-O-tosyl-5-trityl-L-arabinose.

29. The method of claim 1, wherein an L-guanosine or an L-cytosine used for producing L-nucleic acids of step (e) is prepared via silylized heterocycles using peracylated pentose.

30. The method of claim 29, wherein the preparation of L-guanosine comprises 2-N-acetyl-6-O-diphenylcarbamoylguanine.

31. The method according to claim 29, wherein the peracylated pentose is prepared from L-arabinose by epimerization and subsequent derivatization to 1-O-acetyl-2,3,5-tri-O-benzoyl-β-ribofuranoside.

32. The method of claim 1, wherein base-protected nucleosides are formed by protecting the exocyclic amino groups of the L-nucleosides by benzolyation or isobutyrylation.

33. The method of claim 32, wherein the base protected nucleosides and uridine are transformed into their 5'-O-dimethoxytrityl-2-O-trilsopropylsilyl derivatives.

34. The method of claim 1, wherein an L-2'-deoxyadenosine used for producing L-nucleic acids of step (e) is prepared by reduction of L-adenosine.

35. The method of claim 1, wherein an L-2'-deoxyguanosine used for producing L-nucleic acids of step (e) is prepared by reduction of L-guanosine.

36. The method of claim 1, wherein an L-thymidine and an L-2'-deoxycytidine used for producing L-nucleic acids of step (e) is prepared via the intermediate product 3'-5'-di-O-benzoyl-2,2-O-anhydro-L-uridine from L-uridine synthesis.

37. The method of claim 36, wherein L-thymidine is prepared by the following steps:
   (a) transforming 3',5'-di-O-benzoyl-2,2-O-anhydro-L-uridine into 2'-chloro-2'-deoxy-L-uridine;
   (b) transforming 2'-chloro-2'-deoxy-L-uridine into L-2' deoxyuridine by reduction and deblocking; and
   (c) transforming L-2'-deoxyuridine into L-thymidine using formaldehyde and catalytic reduction.

38. The method of claim 36, wherein 3'-5'-di-O-benzoyl-2,2-O-anhydro-L-uridine is transferred into the 4-thio-derivative which is reacted with methanol ammonia by means of pressure into L-2'-deoxycytidine.

39. The method of claim 1, wherein at least one L-nucleoside used for producing L-nucleic acids of step (e) is converted to a protected phosphoramidite.

40. The method of claim 21, wherein the sugar comprises an unbranched or branched polysugar.

* * * * *

```
                              SEQUENCE LISTING

<160> NUMBER OF SEQ ID NOS: 46

<210> SEQ ID NO 1
<211> LENGTH: 96
<212> TYPE: DNA
<213> ORGANISM: Homo sapiens
<220> FEATURE:
<221> NAME/KEY: misc_feature
<222> LOCATION: (1) . . . (96)
<223> OTHER INFORMATION: n = A,T,C or G

<400> SEQUENCE: 1
nnnnnnnnnn nnnnnnnncc gcaaaactta ttagaacctg aatagatatt caggcgaatg      60
tactgagccg ttgtctctgc aggcnnnnnn nnnnnn                               96

<210> SEQ ID NO 2
<211> LENGTH: 101
<212> TYPE: DNA
<213> ORGANISM: Homo sapiens
<220> FEATURE:
<221> NAME/KEY: misc_feature
<222> LOCATION: (1) . . . (101)
<223> OTHER INFORMATION: n = A,T,C or G

<400> SEQUENCE: 2
nnnnnnnnnn nnnnnnnncc gcaaaaacac ctagtgtaac cctccatagc gtgggcgaat      60
gtaaagagct caccccatgc ctgcannnnn nnnnnnnnnn n                        101

<210> SEQ ID NO 3
<211> LENGTH: 100
<212> TYPE: DNA
<213> ORGANISM: Homo sapiens
<220> FEATURE:
<221> NAME/KEY: misc_feature
<222> LOCATION: (1) .. . (100)
<223> OTHER INFORMATION: n = A,T,C or G

<400> SEQUENCE: 3
nnnnnnnnnn nnnnnnnncc gcaaaagcgt ttttcgcata ccgtattcgt tatagggtcg      60
attgtaacga gctctgctcc ctgcaggcnn nnnnnnnnn                           100

<210> SEQ ID NO 4
<211> LENGTH: 100
<212> TYPE: DNA
<213> ORGANISM: Homo sapiens
<220> FEATURE:
<221> NAME/KEY: misc_feature
<222> LOCATION: (1) . . . (100)
<223> OTHER INFORMATION: n = A,T,C or G

<400> SEQUENCE: 4
nnnnnnnnnn nnnnnnnncc gcaaaagtct ttatgacaat cctggtagga cgattgtacc      60
gaagctcaat cacggatctc nnnnnnnnnn nnnnnnnnn                           100

<210> SEQ ID NO 5
<211> LENGTH: 101
<212> TYPE: DNA
<213> ORGANISM: Homo sapiens
```

<220> FEATURE:
<221> NAME/KEY: misc_feature
<222> LOCATION: (1)    (101)
<223> OTHER INFORMATION: n = A,T,C or G

<400> SEQUENCE: 5
nnnnnnnnnn nnnnnnnncc gcaaaacgga gcattgtgat ccgaagtcgc taatcgagtg    60
accgactgta ctgagcatcc ctgcaggcat gcnnnnnnnn n                        101

<210> SEQ ID NO 6
<211> LENGTH: 100
<212> TYPE: DNA
<213> ORGANISM: Homo sapiens
<220> FEATURE:
<221> NAME/KEY: misc_feature
<222> LOCATION: (1) .. (100)
<223> OTHER INFORMATION: n = A,T,C or G

<400> SEQUENCE: 6
nnnnnnnnnn nnnnnnnnnn ctagcaagcc taagcagcag cgaatggaac agtttcccgc    60
aaaaggcttt atgtcatctg nnnnnnnnnn nnnnnnnnnn                          100

<210> SEQ ID NO 7
<211> LENGTH: 102
<212> TYPE: DNA
<213> ORGANISM: Homo sapiens
<220> FEATURE:
<221> NAME/KEY: misc_feature
<222> LOCATION: (1) ... (102)
<223> OTHER INFORMATION: n = A,T,C or G

<400> SEQUENCE: 7
nnnnnnnnnn nnnnnngctc ggtacctatc cctcgccgaa tgtctttgcc attgcaatag    60
accgcaaaag catagttctg cgctgcaggc atgcannnnn nn                       102

<210> SEQ ID NO 8
<211> LENGTH: 58
<212> TYPE: RNA
<213> ORGANISM: Homo sapiens

<400> SEQUENCE: 8
cucgguaccg caaaagcguu uuucgcauac cuauucguua uaggucgauu guaccgag      58

<210> SEQ ID NO 9
<211> LENGTH: 90
<212> TYPE: RNA
<213> ORGANISM: Homossapiens
<220> FEATURE:
<221> NAME/KEY: misc_feature
<222> LOCATION: (1) . . . (90)
<223> OTHER INFORMATION: n = A,U,C or G

<400>  SEQUENCE: 9 nnnnnnnnnn nnnngguacc uagaggcgua uggaaggcgu gguuagaauc cauuagccca    60
uccgcccuua cugcagnnnn nnnnnnnnnn                                     90

<210> SEQ ID NO 10
<211> LENGTH: 90
<212> TYPE: RNA
<213> ORGANISM: Homo sapiens
<220> FEATURE:
<221> NAME/KEY: misc_feature
<222> LOCATION: (1) . . . (90)
<223> OTHER INFORMATION: n = A,U,C or G -continued

```
<400> SEQUENCE: 10
nnnnauucga gcucgguacc aagagggcgu acaguuaaag uaauagccuu gguacacggg      60
uuacggnnnn nnnnnnnnnn nnnnnnnnnn                                      90

<210> SEQ ID NO 11
<211> LENGTH: 90
<212> TYPE: RNA
<213> ORGANISM: Homo sapiens
<220> FEATURE:
<221> NAME/KEY: misc_feature
<222> LOCATION: (1)..(90)
<223> OTHER INFORMATION: n = A,U,C or G

<400> SEQUENCE: 11
nnnnnnnnnn gcucgguacc uuagggugga cggcgugauc auuaaguuca auagcccacc      60
ccgccaacgu cugcnnnnnn nnnnnnnnnn                                      90

<210> SEQ ID NO 12
<211> LENGTH: 89
<212> TYPE: RNA
<213> ORGANISM: Homo sapiens
<220> FEATURE:
<221> NAME/KEY: misc_feature
<222> LOCATION: (1)..(89)
<223> OTHER INFORMATION: n = A,U,C or G

<400> SEQUENCE: 12
nnnnnnnnnn nnnnnnnacc aaugccgcug accaggaugg cguacaguau gugcucuaau      60
agcccuguuc ugcaggcaug cannnnnnn                                       89

<210> SEQ ID NO 13
<211> LENGTH: 90
<212> TYPE: RNA
<213> ORGANISM: Homo sapiens
<220> FEATURE:
<221> NAME/KEY: misc_feature
<222> LOCATION: (1)..(90)
<223> OTHER INFORMATION: n = A,U,C or G

<400> SEQUENCE: 13
nnnnnnnnnn nnnnnnnnnn nnnauggaaa cgagugcaua ggaaggcgua cuuuguaaua      60
gcccuggcac cugcaggcau gnnnnnnnnn                                      90

<210> SEQ ID NO 14
<211> LENGTH: 91
<212> TYPE: RNA
<213> ORGANISM: Homo sapiens
<220> FEATURE:
<221> NAME/KEY: misc_feature
<222> LOCATION: (1)..(91)
<223> OTHER INFORMATION: n = A,U,C or G

<400> SEQUENCE: 14
nnnnnnnnnn gcucgguacc caugcggaga aggcgugcuu cuagaguuag caauagccuc      60
cgugugggac acugcannnn nnnnnnnnnn n                                    91

<210> SEQ ID NO 15
<211> LENGTH: 90
<212> TYPE: RNA
<213> ORGANISM: Homo sapiens
<220> FEATURE:
<221> NAME/KEY: misc_feature
<222> LOCATION: (1)..(90)
<223> OTHER INFORMATION: n = A,U,C or G
```

```
<400> SEQUENCE: 15
nnnnnnnnnn nnucgguacc uuguuuccgg gauggcgugc cguagaugca auagccccgg      60
uuucucuuga cugcnnnnnn nnnnnnnnnn                                      90

<210> SEQ ID NO 16
<211> LENGTH: 90
<212> TYPE: RNA
<213> ORGANISM: Homo sapiens
<220> FEATURE:
<221> NAME/KEY: misc_feature
<222> LOCATION: (1) . . . (90)
<223> OTHER INFORMATION: n = A,U,C or G

<400> SEQUENCE: 16
nnnnauucga gcucgguacc uggauggcgg uacuuaugag guaauagccc gggaacgagc      60 gucggcnnn nnnnnnnnnn nnnnnnnnn                                        90

<210> SEQ ID NO 17
<211> LENGTH: 89
<212> TYPE: RNA
<213> ORGANISM: Homo sapiens
<220> FEATURE:
<221> NAME/KEY: misc_feature
<222> LOCATION: (1)...(89)
<223> OTHER INFORMATION: n=A,U,C or G

<400> SEQUENCE: 17
nnnnauucga gcucgguacc uggauggcgu acuuaugagg uaauagccca ggaacgagcu      60
gucgacnnnn nnnnnnnnn nnnnnnnn                                         89

<210> SEQ ID NO 18
<211> LENGTH: 91
<212> TYPE: RNA
<213> ORGANISM: Homo sapiens
<220> FEATURE:
<221> NAME/KEY: misc_feature
<222> LOCATION: (1). . . (91)
<223> OTHER INFORMATION: n = A,U,C or G

<400> SEQUENCE: 18
nnnnnnnnnn nnucgguacc ccuugaggug gauggcguga cgcugacacu aucuucguca      60
auagcccacc ucugcaggca ugcannnnnn n                                    91

<210> SEQ ID NO 19
<211> LENGTH: 90
<212> TYPE: RNA
<213> ORGANISM: Homo sapiens
<220> FEATURE:
<221> NAME/KEY: misc_feature
<222> LOCATION: (1) . . . (90)
<223> OTHER INFORMATION: n = A,U,C or G

<400> SEQUENCE: 19
nnnnnnncga gcucgguacc ugagggaugg cguagaugcg acuggcacua auagcccuc       60 agauguucgu cugcnnnnnn nnnnnnnnnn                                      90

<210> SEQ ID NO 20
<211> LENGTH: 92
<212> TYPE: RNA
<213> ORGANISM: Homo sapiens
<220> FEATURE:
<221> NAME/KEY: misc_feature
<222> LOCATION: (1) . . (92)
```

<223> OTHER INFORMATION: n = A,U,C or G

<400> SEQUENCE: 20
nnnnnnnnnn ncucgguacc uuugcggcaa uagcccacuu guucnnnnnn nugacaagug    60
gacggcgugc ugcugcaggc augcannnnn nn    92

<210> SEQ ID NO 21
<211> LENGTH: 89
<212> TYPE: RNA
<213> ORGANISM: Homo sapiens
<220> FEATURE:
<221> NAME/KEY: misc_feature
<222> LOCATION: (1) ... (89)
<223> OTHER INFORMATION: n = A,U,C or G

<400> SEQUENCE: 21
nnnnnnnnnn nnncgguacc agccgaaaga aauagcccuu aguccnnnn ncggauugag    60 gauggcguuc ugcaggcaug caagcnnnn    89

<210> SEQ ID NO 22
<211> LENGTH: 89
<212> TYPE: RNA
<213> ORGANISM: Homo sapiens
<220> FEATURE:
<221> NAME/KEY: misc_feature
<222> LOCATION: (1) ... (89)
<223> OTHER INFORMATION: n = A,U,C or G

<400> SEQUENCE: 22
nnnnnnnnnn nnnnnnnacc cgacccucgg ucuuaauagc ccuuauaaga ggauggcgug    60
agaccguaac ugcaggnnnn nnnnnnnnn    89

<210> SEQ ID NO 23
<211> LENGTH: 91
<212> TYPE: RNA
<213> ORGANISM: Homo sapiens
<220> FEATURE:
<221> NAME/KEY: misc_feature
<222> LOCATION: (1) . . . (91)
<223> OTHER INFORMATION: n = A,U,C or G

<400> SEQUENCE: 23
nnnnnnnnnn nnncgguacc agccgaaaga aauagcccuu aguccannnn nncggauuga    60
ggauggcguu cugcaggcau gcaagcnnnn n    91

<210> SEQ ID NO 24
<211> LENGTH: 90
<212> TYPE: RNA
<213> ORGANISM: Homo sapiens
<220> FEATURE:
<221> NAME/KEY: misc_feature
<222> LOCATION: (1) ... (90)
<223> OTHER INFORMATION: n = A,U,C or G

<400> SEQUENCE: 24
nnnnnnnnnn nnnngguacc cacuaugcug uaauagcccu cguaucugag gauggcguac    60
ggcuuagugg cugcannnnn nnnnnnnnn    90

<210> SEQ ID NO 25
<211> LENGTH: 90
<212> TYPE: RNA
<213> ORGANISM: Homo sapiens
<220> FEATURE:
<221> NAME/KEY: misc_feature

```
<222> LOCATION: (1)...(90)
<223> OTHER INFORMATION: n = A,U,C or G

<400> SEQUENCE: 25
nnnnnnnnna gcucgguacc cuugccaaua gccggacacc agnnnnnnnu acguuuccga    60
uggcguggca cugcaggcau gcannnnnnn                                   90

<210> SEQ ID NO 26
<211> LENGTH: 90
<212> TYPE: RNA
<213> ORGANISM: Homo sapiens
<220> FEATURE:
<221> NAME/KEY: misc_feature
<222> LOCATION: (1)...(90)
<223> OTHER INFORMATION: n = A,U,C or G

<400> SEQUENCE: 26
nnnnnnnnnn nnnnnnnnnn nnnacucgug ugcaugcauc aauagcuuac ggaaauguaa    60
gacggcguga cugcaggcau gcaagnnnnn                                   90

<210> SEQ ID NO 27
<211> LENGTH: 90
<212> TYPE: RNA
<213> ORGANISM: Homo sapiens
<220> FEATURE:
<221> NAME/KEY: misc_feature
<222> LOCATION: (1)...(90)
<223> OTHER INFORMATION: n = A,U,C or G

<400> SEQUENCE: 27
nnnaauucga gcucgguacc aauagcccac aaagaaagug gaaggcgugg aagagcuucu    60
cccaannnnn nnnnnnnnnn nnnnnnnnnn                                   90

<210> SEQ ID NO 28
<211> LENGTH: 90
<212> TYPE: RNA
<213> ORGANISM: Homo sapiens
<220> FEATURE:
<221> NAME/KEY: misc_feature
<222> LOCATION: (1)...(90)
<223> OTHER INFORMATION: n = A,U,C or G

<400> SEQUENCE: 28
nnnnnnnnnn nnnnnnnnnn nnacucgugu gcaugcauca auagccuuac ggaaauguaa    60
gacggcguga cugcaggcau gcaagnnnnn                                   90

<210> SEQ ID NO 29
<211> LENGTH: 89
<212> TYPE: RNA
<213> ORGANISM: Homo sapiens
<220> FEATURE:
<221> NAME/KEY: misc_feature
<222> LOCATION: (1)...(89)
<223> OTHER INFORMATION: n = A,U,C or G

<400> SEQUENCE: 29
nnnnnnnnnn ncucgguacc aacuuugcaa uagccuccac ucguagagcu ggagauggcg    60
ugcgaaacac ugcaggcann nnnnnnnn                                     89

<210> SEQ ID NO 30
<211> LENGTH: 88
<212> TYPE: RNA
<213> ORGANISM: Homo sapiens
<220> FEATURE:
```

```
<221> NAME/KEY: misc_feature
<222> LOCATION: (1) . . . (88)
<223> OTHER INFORMATION: n = A,U,C or G

<400> SEQUENCE: 30
nnnnnnnnnn nnnnnnnnnn ugcgugucuc uaugguaaau agcccgguaa uugaugccgg      60
auggcguauc ugcaggcaug caagnnnn                                         88

<210> SEQ ID NO 31
<211> LENGTH: 90
<212> TYPE: RNA
<213> ORGANISM: Homo sapiens
<220> FEATURE:
<221> NAME/KEY: misc_feature
<222> LOCATION: (1) ..... (90)
<223> OTHER INFORMATION: n = A,U,C or G

<400> SEQUENCE: 31
nnnnnnnnnn gcucgguacc ugccguuaau agcccuacca ucgnnnnnnn ngaaugguag      60
gaaggcguaa cugcaggcau gcaagnnnnn                                       90

<210> SEQ ID NO 32
<211> LENGTH: 90
<212> TYPE: RNA
<213> ORGANISM: Homo sapiens
<220> FEATURE:
<221> NAME/KEY: misc_feature
<222> LOCATION: (1).....(90)
<223> OTHER INFORMATION: n = A,U,C or G

<400> SEQUENCE: 32
nnnnnnnnnn nnnnnnnnnn nnnaaacgca ugcugcgucg aauagcccca uucacaaugg      60
gauggcgucg cugcaggcau gcaagnnnnn                                       90

<210> SEQ ID NO 33
<211> LENGTH: 31
<212> TYPE: RNA
<213> ORGANISM: Homo sapiens
<220> FEATURE:
<221> NAME/KEY: misc_feature
<222> LOCATION: (1) . . . (31)
<223> OTHER INFORMATION: n = A,U,C or G

<400> SEQUENCE: 33
nnnnnrgang gcgunnnnaa uagccynnnn n                                     31

<210> SEQ ID NO 34
<211> LENGTH: 31
<212> TYPE: RNA
<213> ORGANISM: Homo sapiens
<220> FEATURE:
<221> NAME/KEY: misc_feature
<222> LOCATION: (1) . . . (31)
<223> OTHER INFORMATION: n = A,U,C or G

<400> SEQUENCE: 34
nnnnnaauag ccynnnnrga nggcgunnnn n                                     31

<210> SEQ ID NO 35
<211> LENGTH: 38
<212> TYPE: RNA
<213> ORGANISM: Homo sapiens

<400> SEQUENCE: 35
cggauggaag gcgugguuag aauccaauag cccauccg                              38
```

<210> SEQ ID NO 36
<211> LENGTH: 100
<212> TYPE: RNA
<213> ORGANISM: Homo sapiens
<220> FEATURE:
<221> NAME/KEY: misc_feature
<222> LOCATION: (1).....(100)
<223> OTHER INFORMATION: n = A,U,C or G

<400> SEQUENCE: 36
gggaauucga gcucgguacc nnnnnnnnnn nnnnnnnnnn nnnnnnnnnn nnnnnnnnnn    60
nnnnnnnnnn nnnnnnnnnn cugcaggcau gcaagcuugg                          100

<210> SEQ ID NO 37
<211> LENGTH: 40
<212> TYPE: DNA
<213> ORGANISM: Homo sapiens

<400> SEQUENCE: 37
ttcattttcg acggccagtg ccaagcttgc atgcctgcag                          40

<210> SEQ ID NO 38
<211> LENGTH: 40
<212> TYPE: DNA
<213> ORGANISM: Homo sapiens

<400> SEQUENCE: 38
gaaacagcta tgaccatgat gggaattcga gctcggtacc                          40

<210> SEQ ID NO 39
<211> LENGTH: 140
<212> TYPE: DNA
<213> ORGANISM: Homossapiens
<220> FEATURE:
<221> NAME/KEY: misc_feature
<222> LOCATION: (1) ... (140)
<223> OTHER INFORMATION: n = A,T,C or G

<400> SEQUENCE: 39
ttcattttcg acggccagtg ccaagcttgc atgcctgcag nnnnnnnnnn nnnnnnnnnn    60
nnnnnnnnnn nnnnnnnnnn nnnnnnnnnn nnnnnnnnnn ggtaccgagc tcgaattccc    120
atcatggtca tagctgtttc                                                140

<210> SEQ ID NO 40
<211> LENGTH: 140
<212> TYPE: DNA
<213> ORGANISM: Homo sapiens
<220> FEATURE:
<221> NAME/KEY: misc_feature
<222> LOCATION: (1) ... (140)
<223> OTHER INFORMATION: n = A,T,C or G

<400> SEQUENCE: 40
gaaacagcta tgaccatgat gggaattcga gctcggtacc nnnnnnnnnn nnnnnnnnnn    60
nnnnnnnnnn nnnnnnnnnn nnnnnnnnnn nnnnnnnnnn ctgcaggcat gcaagcttgg    120
cactggccgt cgaaaatgaa                                                140

<210> SEQ ID NO 41
<211> LENGTH: 140
<212> TYPE: DNA
<213> ORGANISM: Homo sapiens
<220> FEATURE:

<221> NAME/KEY: misc_feature
<222> LOCATION: (1) ... (140)
<223> OTHER INFORMATION: n = A,T,C or G

<400> SEQUENCE: 41
ttcattttcg acggccagtg ccaagcttgc atgcctgcag nnnnnnnnnn nnnnnnnnnn    60
nnnnnnnnnn nnnnnnnnnn nnnnnnnnnn nnnnnnnnnn ggtaccgagc tcgaattccc   120
atcatggtca tagctgtttc                                               140

<210> SEQ ID NO 42
<211> LENGTH: 99
<212> TYPE: DNA
<213> ORGANISM: Homo sapiens
<220> FEATURE:
<221> NAME/KEY: misc_feature
<222> LOCATION: (1) . . . (99)
<223> OTHER INFORMATION: n = A,T,C or G

<400> SEQUENCE: 42
nnnnnnnnnn nnnnnnnnnn ggctcattgc ctgttgccgc aaaatgatat taatcaaaac    60
cgagttcttc ggtcgaatgc tgcaggcatg caagcttgg                          99

<210> SEQ ID NO 43
<211> LENGTH: 100
<212> TYPE: DNA
<213> ORGANISM: Homo sapiens
<220> FEATURE:
<221> NAME/KEY: misc_feature
<222> LOCATION: (1) ... (100)
<223> OTHER INFORMATION: n = A,T,C or G

<400> SEQUENCE: 43
nnnnnnnnnn nnncggtacc gccggagtac cgcaaaacgg gaaaccgaac tagtagatag    60
cgtatactag cgattgtagt ctgcaggcat gcaagcttgg                         100

<210> SEQ ID NO 44
<211> LENGTH: 106
<212> TYPE: DNA
<213> ORGANISM: Homo sapiens
<220> FEATURE:
<221> NAME/KEY: misc_feature
<222> LOCATION: (1) ... (106)
<223> OTHER INFORMATION: n = A,T,C or G

<400> SEQUENCE: 44
nnnnnnnnnn nnnnnnnnnn tgccgtctaa gtgatccagg tgatgaccga atgcctgagc    60
attatcaggc cgcaaaaaga ctgcaggnnn nnnnnnnnn nnnnnn                   106

<210> SEQ ID NO 45
<211> LENGTH: 100
<212> TYPE: DNA
<213> ORGANISM: Homo sapiens
<220> FEATURE:
<221> NAME/KEY: misc_feature
<222> LOCATION: (21)..(80)
<223> OTHER INFORMATION: n = A,T,C, or G

<400> SEQUENCE: 45
ccaagcttgc atgcctgcag nnnnnnnnnn nnnnnnnnnn nnnnnnnnnn nnnnnnnnnn    60
nnnnnnnnnn nnnnnnnnnn ggtaccgagc tcgaattccc                         100

<210> SEQ ID NO 46
<211> LENGTH: 12

```
-continued

<212> TYPE: PRT
<213> ORGANISM: Homo sapiens

<400> SEQUENCE: 46

Tyr Gly Arg Lys Lys Arg Arg Gln Arg Arg Pro
1               5                   10
```